(12) United States Patent
Ho et al.

(10) Patent No.: US 8,573,211 B2
(45) Date of Patent: Nov. 5, 2013

(54) RESPIRATORY MASK SEAL AND MASK USING SAME

(75) Inventors: Peter Chi Fai Ho, Pittsburgh, PA (US); Lance Busch, Trafford, PA (US); Eugene N. Scarberry, Trafford, PA (US); Jason P. Eaton, Hunker, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 13/370,407

(22) Filed: Feb. 10, 2012

(65) Prior Publication Data

US 2012/0138062 A1    Jun. 7, 2012

Related U.S. Application Data

(63) Continuation of application No. 11/266,808, filed on Nov. 3, 2005, now Pat. No. 8,127,764.

(60) Provisional application No. 60/625,469, filed on Nov. 5, 2004.

(51) Int. Cl.
*A62B 18/08* (2006.01)
*A62B 18/02* (2006.01)

(52) U.S. Cl.
USPC ............ 128/206.24; 128/200.24; 128/205.25; 128/206.21

(58) Field of Classification Search
USPC ................. 128/857, 200.24, 201.22, 201.23, 128/203.29, 205.25, 206.12, 206.13, 128/206.14, 206.18, 206.21, 206.23, 128/206.24, 206.25, 206.28, 207.13
See application file for complete search history.

(56) References Cited

U.S. PATENT DOCUMENTS

| | | | |
|---|---|---|---|
| 3,848,605 A * | 11/1974 | Harautuneian et al. .. | 128/207.15 |
| 4,971,051 A | 11/1990 | Toffolon | |
| 5,243,971 A | 9/1993 | Sullivan | |
| 5,540,223 A | 7/1996 | Starr | |
| 5,647,357 A | 7/1997 | Barnett | |
| 6,005,041 A | 12/1999 | Cook | |
| 6,123,071 A | 9/2000 | Bethon-Jones | |
| 6,397,847 B1 * | 6/2002 | Scarberry et al. ........ | 128/206.24 |
| 6,420,475 B1 | 7/2002 | Chen | |
| 6,467,483 B1 | 10/2002 | Kopacko | |
| 6,536,435 B1 | 3/2003 | Fecteau | |
| 6,584,977 B1 * | 7/2003 | Serowski ................. | 128/206.24 |
| 6,895,965 B2 * | 5/2005 | Scarberry et al. ........ | 128/206.24 |
| 6,978,782 B2 | 12/2005 | Tayebi | |
| 2002/0040978 A1 | 4/2002 | Narayan | |
| 2004/0118406 A1 | 6/2004 | Lithgow | |

FOREIGN PATENT DOCUMENTS

| | | |
|---|---|---|
| JP | 2004512076 | 4/2004 |
| WO | WO0234108 A2 | 5/2002 |

* cited by examiner

*Primary Examiner* — Annette Dixon
(74) *Attorney, Agent, or Firm* — Michael W. Haas

(57) ABSTRACT

A seal and a mask using a seal that includes a first end portion adapted to be coupled to a seal support, a second end portion adapted for sealing engagement with a face of a user, and a sidewall extending between the first end portion and the second end portion. The first end portion, second end portion, sidewall, or any combination thereof is formed from an elastomeric material having an elongation of at least 1000%. The seal preferably formed from a unitary piece of elastomeric material.

14 Claims, 20 Drawing Sheets

RESPIRATORY MASK SEAL AND MASK USING SAME

CROSS-REFERENCE TO RELATED APPLICATIONS

This application is a Continuation of U.S. patent application Ser. No. 11/266,808, filed Nov. 3, 2005, now granted as U.S. Pat. No. 8,127,764 on Mar. 6, 2012, which claims priority under 35 U.S.C. §119(e) from provisional U.S. patent application No. 60/625,469, filed Nov. 5, 2004, the contents of which are incorporated herein by reference.

BACKGROUND OF THE INVENTION

1. Field of the Invention

The present invention relates to a flexible, elastic seal adapted to contact a patient's face and create a sealed interface with an airway of a patient, and to a respiratory mask using such a seal.

2. Description of the Related Art

A variety of respiratory masks are known that have flexible seals and that cover the nose, mouth, or both of a human patient. The seal on a respiratory mask, which is also commonly referred to as a cushion, is intended to create a seal against the patient's face. Because of the sealing effect that is created, gases can be provided at a positive pressure within the mask for delivery to the airway of the patient.

The uses for such masks range from high altitude breathing, e.g., aviation applications, to mining and fire fighting applications, to various medical diagnostic and therapeutic applications. For example, such masks are used in the delivery of continuous positive airway pressure (CPAP) or a variable airway pressure to an airway of a patient. Examples of variable positive airway pressure systems include a conventional ventilator, which provides a non-invasive ventilation, a bi-level pressure support system, which varies the pressure delivered to the patient with the patient's respiratory cycle, an auto-titrating pressure support system, which varies the delivered pressure with the monitored condition of the patient, and a proportional positive airway pressure (PPAP) support system, which varies the delivered pressure with the patient's effort. Typical pressure support therapies are provided to treat a medical disorder, such as sleep apnea syndrome, in particular, obstructive sleep apnea (OSA), Cheynes-Stokes respiration, and congestive heart failure.

A requisite of such respiratory masks is that they provide an effective seal against the patient's face to prevent leakage of the gas being supplied. Commonly, in conventional mask configurations, a good mask-to-face seal has been attained in many instances only with considerable discomfort to the patient. This problem is most crucial because such masks are typically worn for an extended period of time. One concern in such a situation is that a patient may avoid wearing an uncomfortable mask, defeating the purpose of the prescribed pressure support therapy.

Numerous attempts have been made to provide a seal that is effective, i.e., provides a seal with the surface of the patient that minimizes leak, and that is comfortable. U.S. Pat. No. 5,243,971, for example, teaches a bubble-type of patient interface in which the seal has a convex surface that engages the user. This patent teaches that the seal is a distentable membrane molded from an elastic plastic material. The convex surface of the seal deforms inward on itself as the user applies the seal on his or her face. It is believed that deforming the seal provides an adequate mask-to-face seal for the application of a positive pressure therapy. It can, thus, be appreciated, that this seal configuration uses the shape of the seal and its ability to deform inward from the original convex shape, in combination with the pressure provided inside the seal by the pressure support system, to provide the necessary seal against the patient's face so that the seal can fit a wide variety of patients, i.e., patient's having different facial sizes and structures.

Rather than rely on the ability of the material forming the seal to deform such that a good seal is created, other seals rely on the type of material forming the seal to create an effective mask-to-patient seal. For example, U.S. Pat. No. 5,647,357 teaches forming the seal from a gel material having a durometer in a range of 20 to 45 on the Shore 000 scale. This type of gel material is very soft to the touch, providing a comfortable interface between the patient and the respiratory mask. The resiliency of the gel material ensures that leaks at the seal-patient interface are minimized. However, these gel cushion are sometimes perceived as bulky or heavy.

Still others have attempted to provide a good mask-to-patient seal through the use of multiple flaps at the patient contacting portion of the seal. See, for example, U.S. Pat. No. 4,971,051. While each of these different types of mask seals may be effective is some patients, there still exists a need for an improved seal for a respiratory mask that is 1) comfortable to wear over an extended period of time, 2) provides a seal that minimizes gas leakage at the mask-patient interface, and 3) fits a wide variety of facial structures and sizes, so that a commonly sized and style of seal can be used on many different patients.

SUMMARY OF THE INVENTION

Accordingly, it is an object of the present invention to provide a respiratory mask seal that overcomes the shortcomings of conventional seals. This object is achieved according to one embodiment of the present invention by providing a seal that includes a first end portion adapted to be coupled to a seal support, a second end portion adapted for sealing engagement with a face of a patient, and a sidewall extending between the first end portion and the second end portion. The first end portion, second end portion, sidewall, or any combination thereof is formed from an elastomeric material having an elongation in a range of 1000% or greater. The seal preferably formed from a unitary piece of elastomeric material.

It is yet another object of the present invention to provide a respiratory mask that includes the above-described seal. In addition to the seal, the mask includes a seal support and a mask body. A further embodiment of the present invention adds a retaining member and a conduit coupling member to the mask. The mask body preferably is a generally rigid formed structural shell. The seal includes a seal support that is relatively rigid. The seal support comprises a peripheral wall portion having an annular base or inner end configured substantially similar to the annular surface of the mask body to which it may be fixedly attached.

The seal includes an opening in the second end portion. Due to the super elastic nature of the super elastomeric material, it is possible to reduce this opening to a minimum. This allows the second end portion of the seal to wrap around the nasal features, thereby reducing if not eliminating leakage of gas at the patient-seal interface. The opening in the second end portion of the seal may have a slightly thickened wall section, be reinforced or stiffened, and/or include a web piece separating the nares to reduce the potential for noise due to vibration of the edge of the seal. Also, the seal support, when desired, is only required at the side of the mask and there is no need for a flap-like feature found in conventional seals. The seal support can include a thicker wall section of the same material as the seal, a separate relatively rigid piece, or can be integral with the mask body to stiffen or reinforce the seal.

The elastomeric material of the seal is preferably a thermoplastic gel material. The thermoplastic gel material allows the seal to be formed with an injection molding process. Unlike the early gel technology, the gel material does not need to be enclosed within a polyurethane capsule. The forming process of such a polyurethane capsule restrains the geometry of the cushion. The invention will eliminate such limitation. In a preferred embodiment, the seal is also not tacky or sticky, but is smooth and silky to the touch.

The thermoplastic gel material is from the family of the styrene block copolymer thermoplastic elastomers, which are commercially available in many forms. According to an exemplary embodiment of the present invention, the following seal includes the following additional physical properties so that the seal provides the desired performance and feel in this mask application with the given geometry:

Hardness (ASTM D2240)-20 to 30 shore 00 range,
300% Modulus (ASTM D412)-10 to 15 PSI, and
Tear Strength (ASTM D624)-40 to 50 PLI range.

Due to the low modulus of the thermoplastic gel material, the seal may require additional support around the perimeter on the sidewall to stiffen the support. This reinforcement can be achieved by a prominent thick side section or by an over molded supporting ring. The thermoplastic gel material makes advance processing techniques, such as two-shot molding and over-molding possible.

One of the side effects of the low modulus of the thermoplastic gel material is that the thin section may have a resonance effect in respond to any pressure differential. To avoid this result, the present invention contemplates providing sections of the seal with differentiated wall thickness in specific pattern to diminish or reduce the resonance effect.

The thermoplastic gel material eliminates the polyurethane capsule, which is a barrier between the gel material and the patient. The removal of the barrier allows the gel to deform directly in response to the facial properties of the patient. The polyurethane capsule complicates the manufacturing process and limits the geometry of the cushion. The thermoplastic gel material allows complex contour for the cushion design. It does not require a material barrier.

The nature of the thermoplastic gel material allows it to be formed economically using a simple injection molding process, which is compatible to advance insert and over molding technologies that opens up many possible configuration improvements.

Additionally, a system for delivering a flow of gas to a patient is provided that includes a gas flow generating device capable of producing a flow of gas and a conduit having a first end portion operatively coupled to the gas flow generating device and a second end portion. The conduit carries the flow of gas from the gas flow generating device. The system includes a respiratory mask operatively coupled to the second end portion of the conduit.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
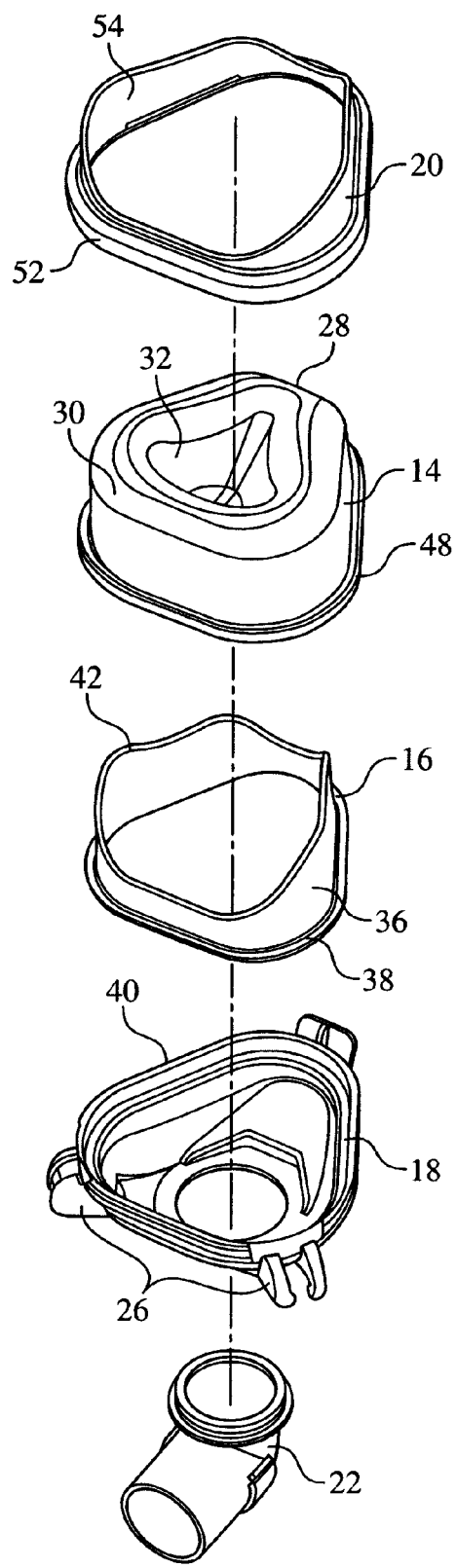
FIG. 1 is an exploded view of a respiratory mask assembly according to the principles of the present invention.
Figure 2:
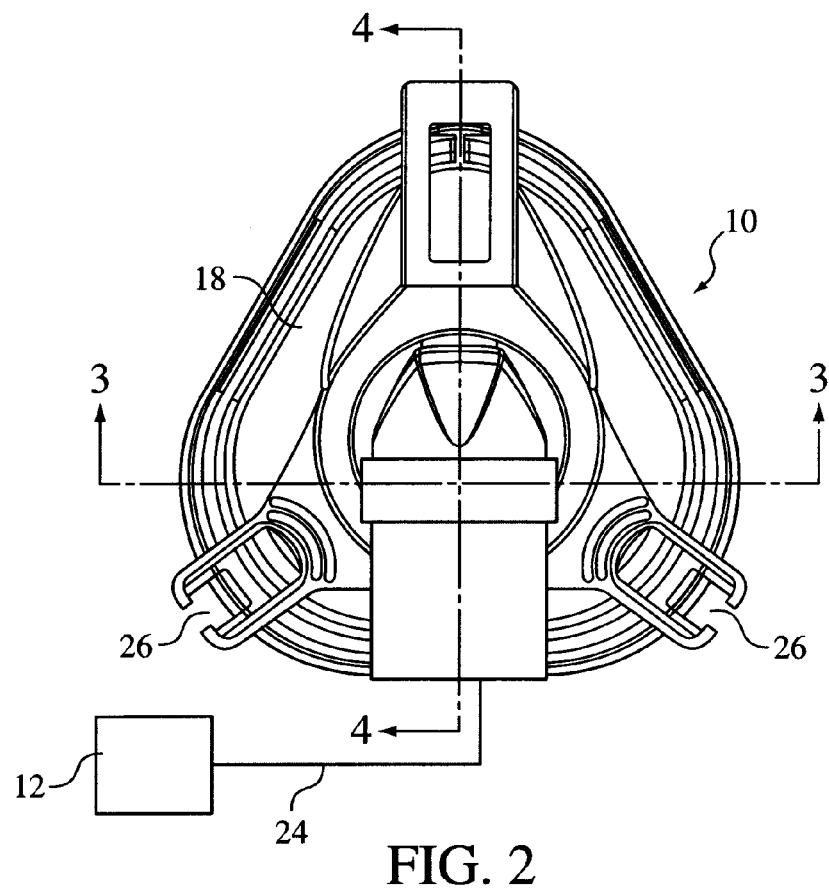
FIG. 2 is a front view of the mask assembly of FIG. 1.
Figure 3:
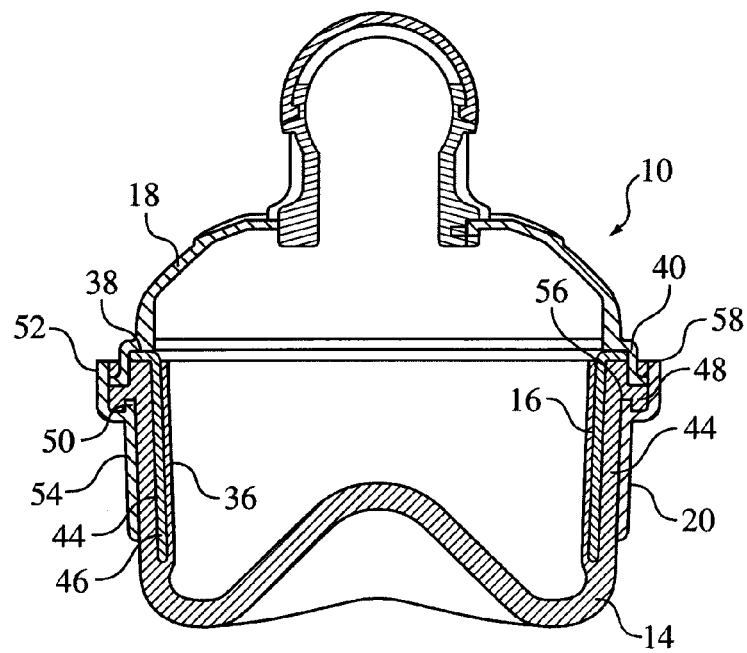
FIG. 3 is a cross-sectional view of the mask assembly taken along 3-3 of FIG. 2.
Figure 4:
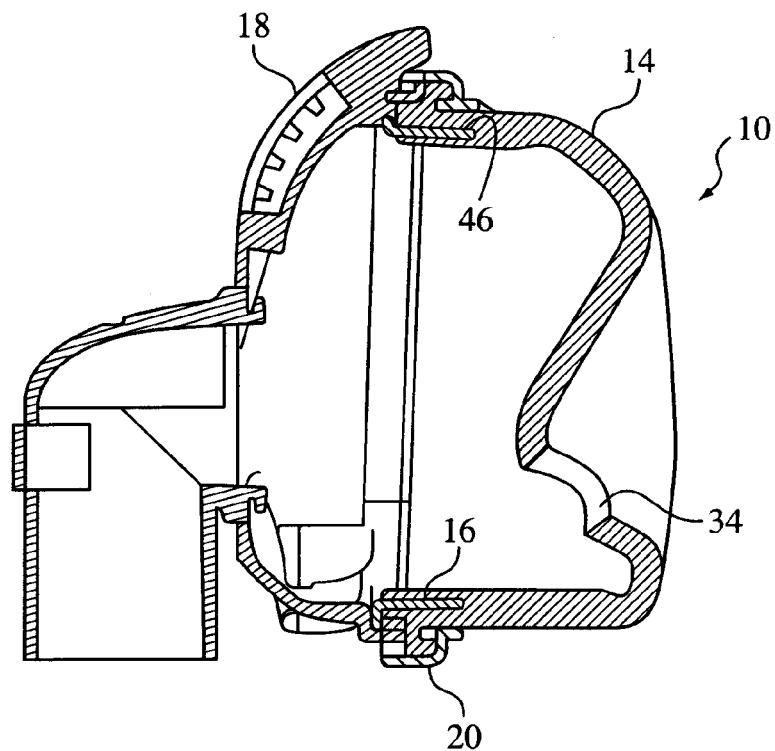
FIG. 4 is a cross-sectional view of the mask assembly taken along 4-4 of FIG. 2.

FIGS. 1-4 illustrate an exemplary embodiment of a respiratory mask 10 according to the principles of the present invention. Respiratory mask 10 functions as a patient interface device that communicates a flow of breathing gas between the patient's airway and a pressure/flow generating device 12, such as a ventilator, CPAP device, or variable pressure device. Examples of a pressure support system that generates a variable pressure include an auto-titrating device, proportional assist ventilation (PAV) device, proportional positive airway pressure (PPAP) device, C-Flex device, Bi-Flex device, or a BiPAP® device manufactured and distributed by Respironics, Inc. of Murrysville, Pa., in which the pressure provided to the patient varies with the patient's respiratory cycle so that a higher pressure is delivered during inspiration than during expiration, or other pressure support devices. The pressure generating device is shown schematically in FIG. 2. It is to be understood that the mask of the present invention is suitable for use with any non-invasive pressure support system or ventilator system. This includes single-limb or multi-limb circuits.

Communicating a flow of breathing gas between the patient's airway and a pressure generating device includes delivering a flow of breathing gas to the patient from the pressure/flow generating device via a patient circuit and exhausting a flow of gas from the patient to ambient atmosphere. In a single-limb patient circuit, an exhaust vent is provided at or near the patient interface device. The exhaust vent in single-limb circuit is typically an opening or plurality of openings on or near the patient interface device to allow gas to exhaust from the system without any active control by the pressure support system over the rate of exhaust flow. In a dual-limb patient circuit, the exhaust vent is typically provided at the end of the expiratory leg of the patient circuit distal from the patient. Typically, the exhaust vent in a dual-limb circuit is provided in the ventilator or pressure support device and is actively controlled.

Respiratory mask 10 of the present invention includes a seal 14, which contacts the patient's face, a seal support 16, a mask body 18, a retaining member 20, and a conduit coupling member 22. In an exemplary embodiment of the present invention, conduit coupling member 22 is freely rotatably relative to mask body 18 and is connectable to a conduit 24, which is connectable to the pressure/flow generating device 12. Conduit 24 is also conventionally referred to as a patient circuit. Conduit coupling member 22 can be elbow shaped, strait, or have any configuration suitable to connect a patient circuit to the mask. Mask body 18 preferably is a generally rigid shell having a peripheral annular surface 40.

Respiratory mask 10 shown is a nasal mask, although it is to be understood that the invention contemplates a oral/nasal that covers the nose and mouth, or full face mask that covers a larger portion of the user, specifically the user's face. As is conventional, the mask body also includes a fastening means 26 such as tabs, snaps, or the like, which may be connected to headgear straps (not shown) for retaining the mask on the patient's face. The present invention contemplates that the headgear for use with the present invention can be any headgear that has the ability to attach the mask on the user, i.e., any configuration, shape, size, material, etc. can be used for the headgear without deviating from the principles of the present invention.

Seal 14 has a first end portion 28 and a second end portion 30 generally opposite the first end portion with a nose receiving area 32 defined therebetween. Seal 14 is sized such that at least the distal end portion of the patient's nose is disposed within nose receiving area 32 when mask 10 is positioned on the patient's face. Nose receiving area 32 includes at least one hole 34 defined through the seal communicating with the patient's nares when the mask is properly positioned on the patient.

Seal support 16 is preferably a semi-rigid material such as plastic, ABS, EVA copolymer, polypropylene, HDPE, PE, PVC, or a higher durometer elastomer, such as polyurethane. Seal support 16 comprises a peripheral wall portion 36 having an annular base 38 (or inner end) configured substantially similar to annular surface 40 of mask body 18 to which it is attached. Peripheral wall portion 36 further establishes an outer end 42 generally opposite annular base 38. Outer end 42 defines a generally annular contoured surface that approximates the surface contours of a patient's facial structure in the areas of the bridge of the nose, the cheeks adjacent the nose, the space intermediate the nose and upper lip, and the intervening areas contiguous to these. It should be understood that for a full face mask, the sealing surface would be contoured to accommodate the patient's chin rather than the area intermediate the nose and the upper lip.

Seal 14 preferably has sections with differential wall thickness. For example, sidewalls 44 of seal 14 are preferably thicker than nose receiving cavity area 32. In the embodiment shown in FIGS. 1-4, sidewalls 44 include an annular pocket 46 for receiving seal support 16. In the exemplary illustrated embodiment, seal 14 and seal support 16 attach to the mask body 18 by means of retaining member 20. Seal 14 further includes an annular base 48 having an outer groove 50 for receiving the retaining member.

Retaining member 20 is preferably a unitary member formed from a relatively rigid material, such as plastic. Retaining member 20 includes an annular retaining portion 52 and a sidewall portion 54. Sidewall portion 54 of retaining member 20 is contoured in a manner similar to the seal support discussed above. The present invention contemplates that the sidewall can be eliminated. Seal support 16 inserts within seal 14, and an inner annular portion 56 of annular retaining portion 52 of the seal support inserts into outer groove 50 of seal 20. An outer annular portion 58 of annular retaining portion 52 mounts over seal 14 to attach the seal to mask body 18.

Seal 14 is preferably formed from a unitary piece of superelastic material, such as an elastomeric material or, more specifically, a thermoplastic gel material, which is also referred to as a thermoplastic elastomer gel or "TPE gel". The thermoplastic gel material preferably has the following properties:

Hardness (ASTM D2240)-10 to 50 Shore 00 range;
Elongation (ASTM D412)-1000% to 1800% range;
300% Modulus (ASTM D412)-10 to 15 PSI; and
Tear Strength (ASTM D624)-40 to 50 PLI range.

Each of these properties is discussed briefly below. In a preferred embodiment, the seal is also not tacky or sticky, but is smooth and silky to the touch.

1. Hardness

Hardness is a characteristic of a solid material that expresses its resistance to permanent deformation. It is primarily, in engineering and metallurgy, expressed as indentation hardness, which characterizes a material's resistance to permanent, and in particular plastic, deformation. It is usually measured by loading an indenter of specified geometry onto the material and measuring the dimensions of the resulting indentation. Hardness can be measured in a number of methods. The most common method for measuring the hardness of elastomer is the Shore method.

Shore hardness is a measure of the resistance of material to indentation by the spring-loaded indenter. The higher the number, the greater the resistance. The Shore hardness is measured with an apparatus known as a Durometer and consequently is also known as "Durometer hardness." The hardness value is determined by the penetration of the Durometer indenter foot into the sample. The American Society for Testing and Materials ("ASTM") test number is ASTM D2240, while the analogous ISO test method is ISO 868.

The hardness testing of plastics is most commonly measured by the Shore (Durometer) test. It measures the resistance of the plastic toward indentation, providing an empirical hardness value that doesn't correlate to other properties or fundamental characteristics. Shore Hardness, measuring in different scales such as Shore D, Shore A or Shore 00, is the preferred method for rubbers/elastomers and is also commonly used for "softer" plastics. The Shore 00 scale is used for "softer" rubbers while the Shore D scale is used for 'harder' ones. The Shore 00 Hardness is the relative hardness of elastic materials, such as rubber or soft plastics, and is determined with an instrument called a Shore 00 durometer. If the indenter completely penetrates the sample, a reading of 0 is obtained, and if no penetration occurs, a reading of 100 results. The reading is dimensionless. In the present invention, the seal has a hardness, measured using the ASTM D2240 standard, in a range of 10 to 50 using the Shore 00 scale.

2. Elongation

Elongation is defined as the length at breaking point expressed as a percentage of its original length, i.e. length at rest. For example, if a rubber reaches twice its length before breaking, its elongation is 100%. The seal of the present invention preferably has an elongation, measured using the ASTM D412 standard, of at least 1000%. In an exemplary, presently preferred embodiment, the seal has an elongation in a range or 1000% to 1800%. That is, the seal material of the present invention will stretch 10 to 18 times its original length before breaking.

3. Modulus

In materials science, modulus (or elastic modulus) is a measure of the stiffness of a material. It is also known as Young's modulus. In solid mechanics, Young's modulus or modulus of elasticity, and also elastic modulus, is a measure of the stiffness of a given material. It is defined as the limit for small strains of the rate of change of stress with strain. This can be experimentally determined from the slope of a stress-strain curve created during tensile tests conducted on a sample of the material.

The Young's modulus makes it possible to calculate the behavior of a material under a load. For instance, it can be used to predict the amount a wire will extend under tension, or to predict the load at which a thin column will buckle under compression. Some calculations also require the use of other material properties, such as the shear modulus, density or Poisson's ratio.

For many materials, Young's modulus is a constant over a range of strains. Such materials are called linear, and are said to obey Hooke's law. Examples of linear materials include steel, carbon fiber, and glass. Rubber is a non-linear material. Modulus is measured as the force per unit area required to extend a rubber to a stated percentage of its original length e.g. 100%, 200%, or 300% (the modulus in rubber is non-linear). It is often written as 100% Modulus expressed in PSI. The seal material of the present invention preferably has a 300% Modulus, as measured by the ASTM D412 standard, in a range of 10 to 15 PSI.

4. Tear Strength

Tear strength is measured as the force required to tear a standard test piece. The standard test pieces are designed to produce weak points where a tear is initiated. Values are frequently reported in terms of PLI (pounds per linear inch). The seal material of the present invention preferably has a tear strength, as measured by the ASTM D624 standard, in a range of 40 to 50 PLI.

Figure 5:
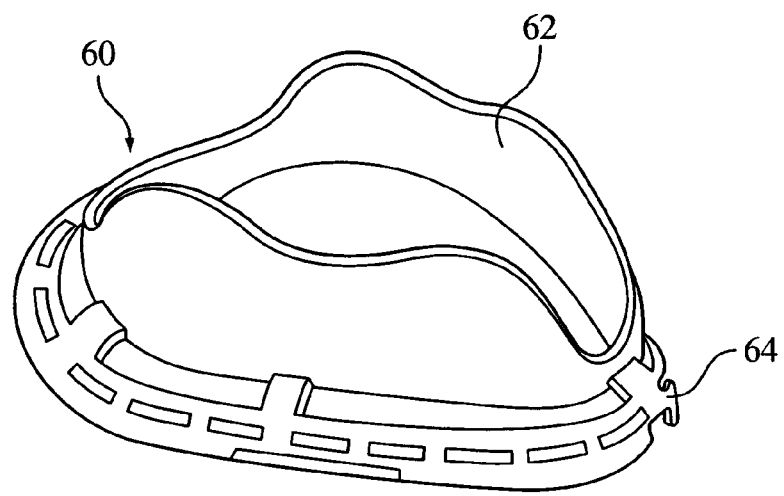
FIG. 5 is a perspective view of an integrated seal support/retaining member according to another embodiment of the present invention.
Figure 6:
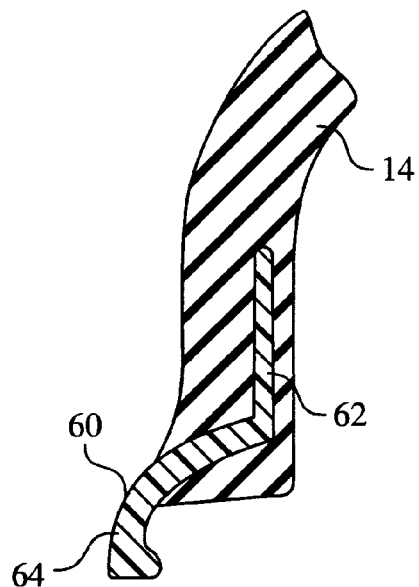
FIG. 6 is a cross-sectional view of a portion of the integrated seal support/retaining member of FIG. 5.

Further alternative exemplary illustrations of a seal assembly according to the principles of the present invention are shown in FIGS. 5-9. More specifically, FIGS. 5 and 6 show an integrated seal support/retaining member 60 molded in one-piece. The integrated seal support/retaining member 60 performs the function of both the seal support and the retaining member while able to use existing mask bodies, i.e., to attach to existing mask shells. As with the previous embodiment for the seal support, seal support/retaining member 60 includes a peripheral wall 62 having a distal edge portion that is contoured to correspond, in general, to the human facial features that will lie under the seal when the mask is worn by a patient. A retaining portion 64 attaches to the mask body by means of a snap-fit engagement of the periphery of the retaining portion with a periphery of the mask body.

In this embodiment, seal 14 is molded directly onto seal support/retaining member 60 so that the seal and the seal support/retaining member effectively form a single component. This provides a strong attachment between the seal and the retaining member. This also allows for easy attachment and detachment of the entire seal assembly, which includes the seal and the seal attachment means, i.e., the seal support/retaining member, onto or from the mask body. It should be noted that the present invention contemplates eliminating the seal support portion of the seal support/retaining member.

Figure 7:
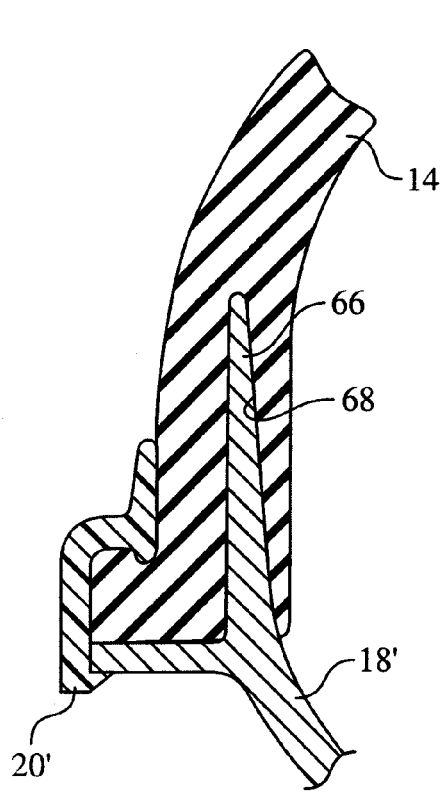
FIG. 7 is a cross-sectional view of an integrated seal support/mask body according to an alternative embodiment of the present invention.
Figure 8:
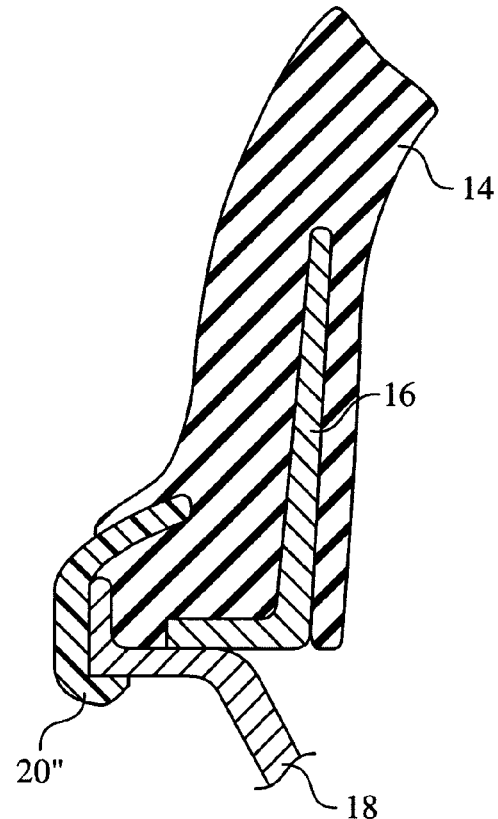
FIG. 8 is a cross-sectional view of a retaining member, embedded seal support, and mask body according to another embodiment of the present invention.
Figure 9:
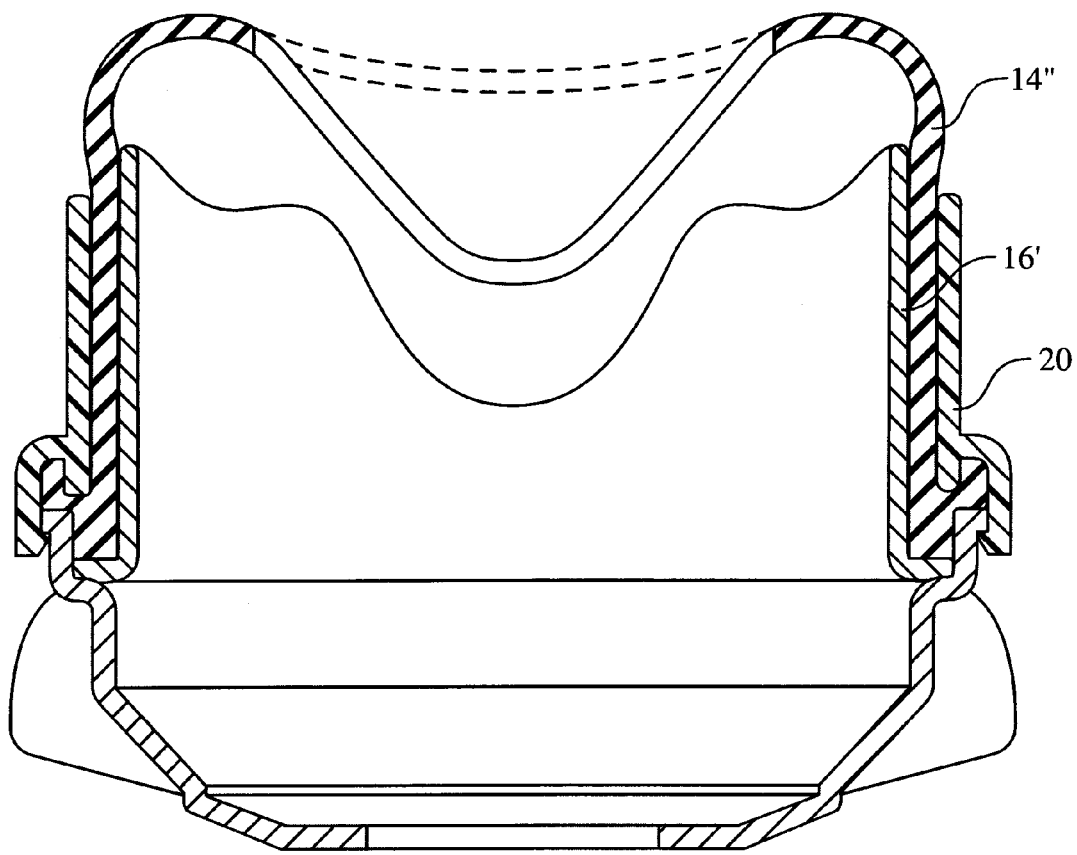
FIG. 9 is a cross-sectional view of yet another embodiment of the mask assembly according to the principles of the present invention.

FIGS. 7-9 illustrate further alternative configurations for attaching the seal to the mask body and for providing structural support for the portion of the seal proximate to the mask body. In the embodiment shown in FIG. 7, seal 14 is attached to mask body 18' via a retaining member 20'. In this embodiment, the retaining member is a separate component from the seal and attaches the seal to the periphery of the mask body as discussed above. Structural support for the seal is provided by means of a support protrusion 66 extending from mask body 18'. The seal includes a channel 68 that receives support protrusion 66. The embodiment shown in FIG. 8, is similar to that of FIGS. 1-4 except that the seal is molded unto retaining member 20" rather than providing these as separate components. FIG. 9 shows an embodiment in which a seal support 16' is not provided in a groove defined in the seal. Instead, seal support 16' is provided external to, i.e., outside, seal 14" on a side opposite retaining member 20.

It should be understood that the techniques for attaching the seal to the mask body and for providing structural support for the seal shown in FIGS. 1-9 and discussed above do not represent all of the possible ways these two functions can be accomplished. Thus, the present invention is not intended to be limited to the embodiments shown. In addition, the seal attaching and supporting functions shown in these figures can be combined in any fashion.

FIGS. 10-32 illustrate various configurations and embodiments for the seal of the present invention. It should be noted that the present invention contemplates attaching the seals shown in these embodiments to the mask body using any of the techniques noted above, as well as any other techniques. All of the seal embodiments shown in these figures and discussed herein preferably include one or more of the properties of seal 14 discussed above, i.e., hardness, elongation, modulus, and tear strength. The present invention also contemplates that the various configurations and embodiments for the seals shown in FIGS. 10-32 apply to a nasal seal, a nasal/oral seal, or a full face seal.

Figure 10:
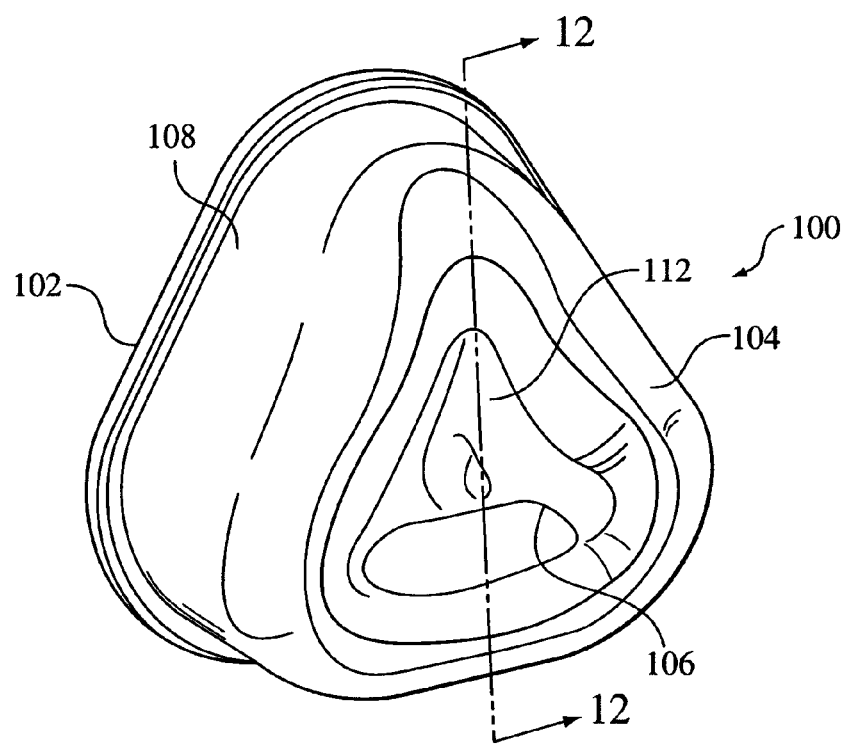
FIG. 10 is a front perspective view of one embodiment for a seal according to the principles of the present invention.
Figure 11:
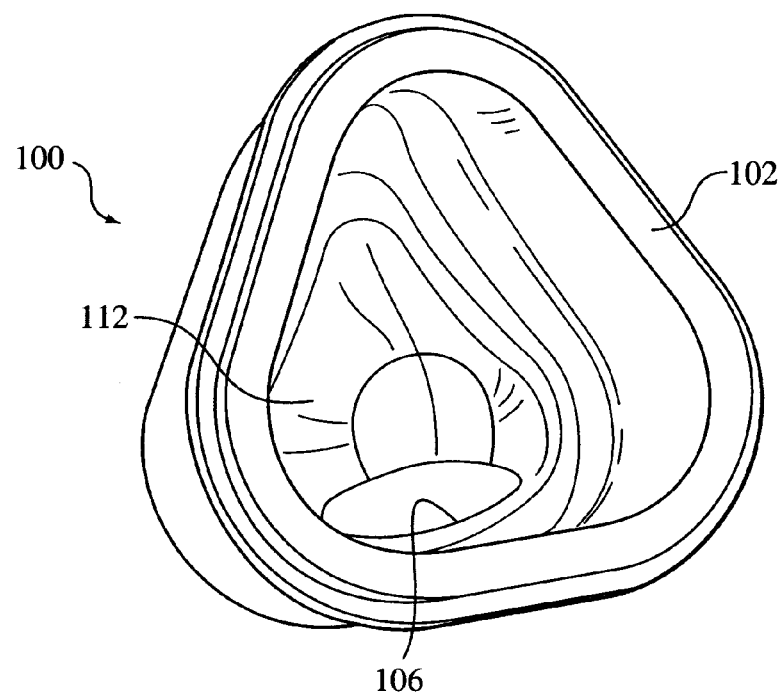
FIG. 11 is a rear perspective of the seal of FIG. 10.
Figure 12:
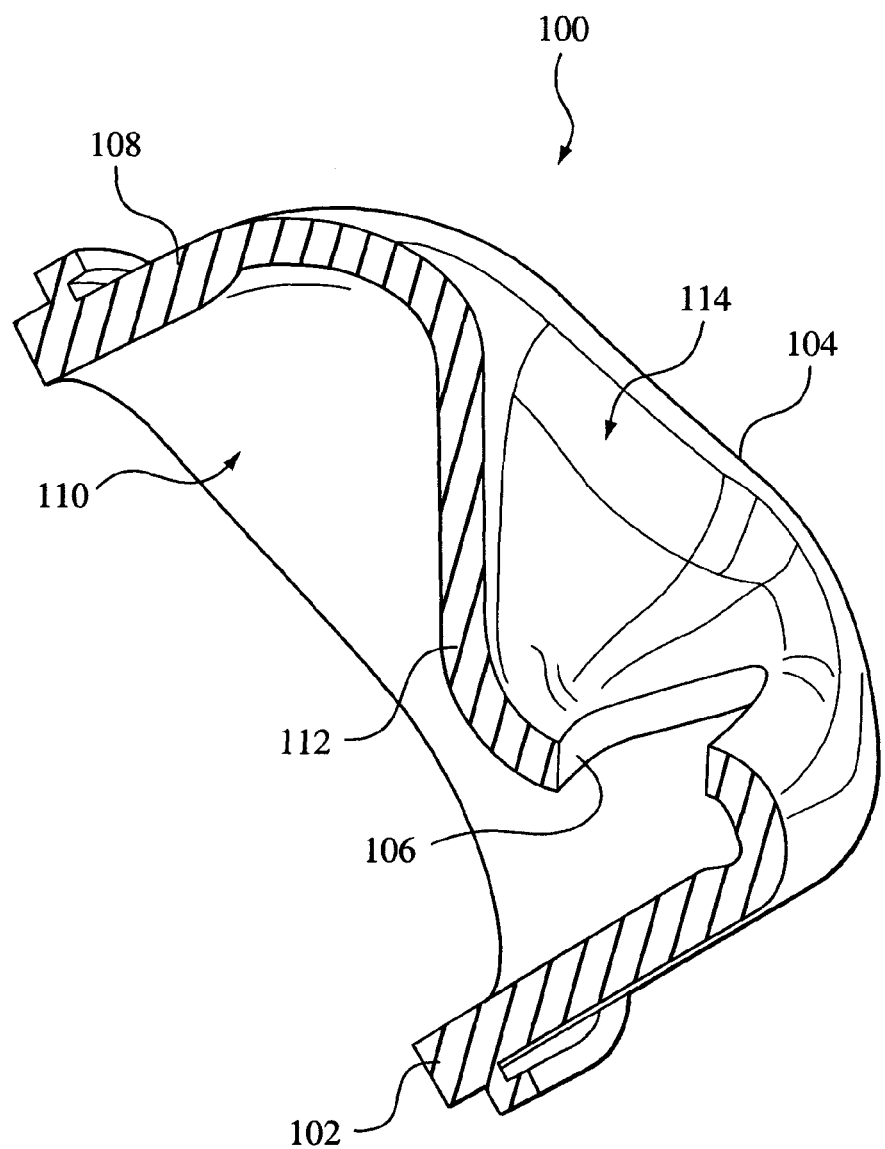
FIG. 12 is a cross-sectional view of the seal taken along line 12-12 of FIG. 10.

FIGS. 10-12 illustrate a seal 100 that is substantially similar to seal 14 of FIGS. 1-4. Seal 100 has a generally triangular shape and is defined from a unitary piece of material. Seal 100 includes a first end portion 102 adapted to be coupled to a mask body, a seal support, retaining member, or any combination thereof. Seal 100 also has a second end portion 104 adapted for sealing engagement with a face of a patient. A single opening 106 is defined in second end portion. A sidewall 108 extends between the first end portion and the second end portion. Opening 106 communicates an airway of the patient, such as the nares, with a chamber 110 defined by the seal.

Second end portion 104 of seal 100 includes a flap 112 that overlies a substantial portion of the user's nose. Flap 112 is configured to provide a nose receiving recess 114 at the second end portion of the seal. The super-elastic nature of the seal, and, in particular, flap 112, allows the flap to readily conform to a variety of differently sized and shaped noses. The super-elastic nature of the seal also allows opening 106 to be made relatively small, leaving a large area at the second end portion of the seal to contact the user, thereby minimizing leakage of gas at the patient-seal interface. In addition, the low durometer of the seal provides a very soft, silky, and comfortable interface with the user's skin, which is especially important given the sensitivity of the tissue that the seal contacts and the length of time that some masks are worn by the patient. These aspects of the present invention improve patient compliance with the prescribed pressure support therapy and allows a common seal to fit a wide variety of patients.

Figure 13:
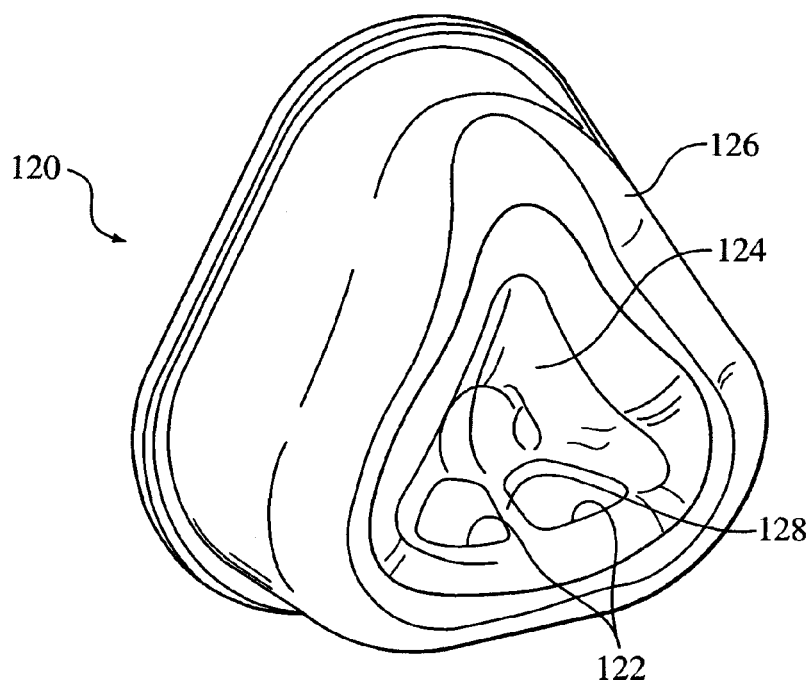
FIG. 13 is a front perspective view of a further embodiment for a seal according to the principles of the present invention.
Figure 14:
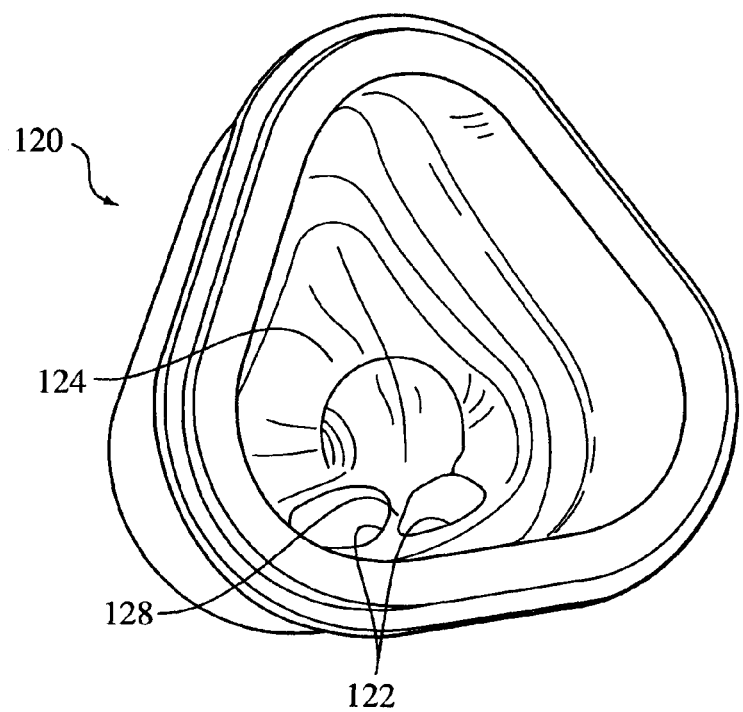
FIG. 14 is a rear perspective of the seal of FIG. 13.
Figure 15:
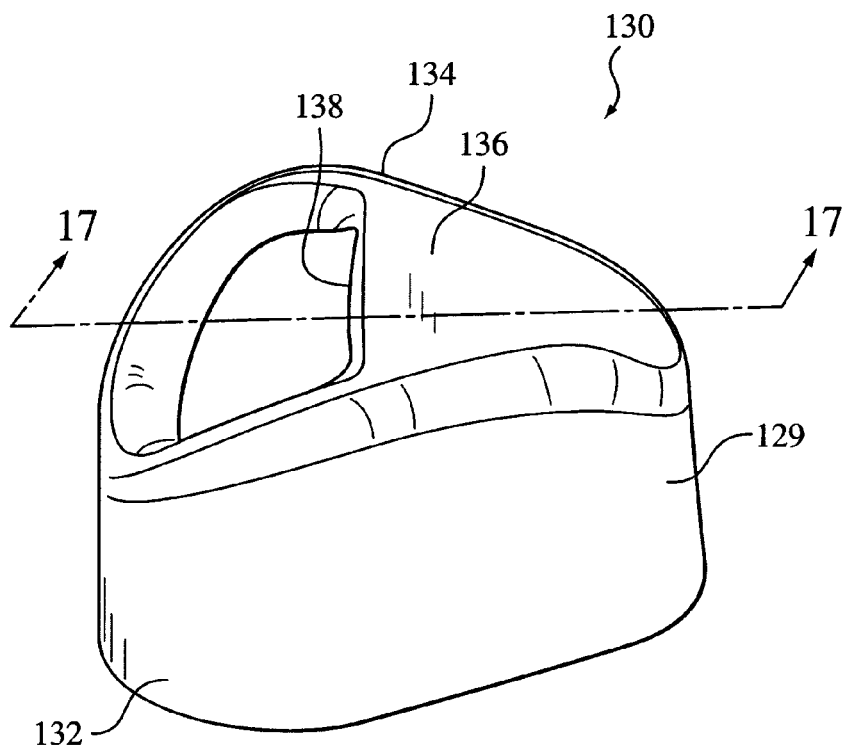
FIG. 15 is a side perspective view of a still further embodiment for a seal according to the principles of the present invention.
Figure 16:
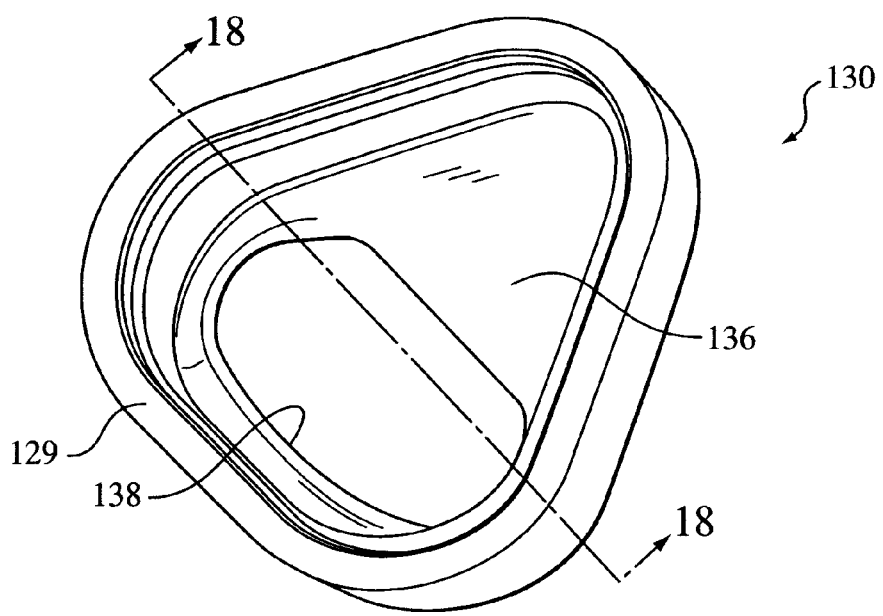
FIG. 16 is a rear perspective of the seal of FIG. 15.
Figure 17:
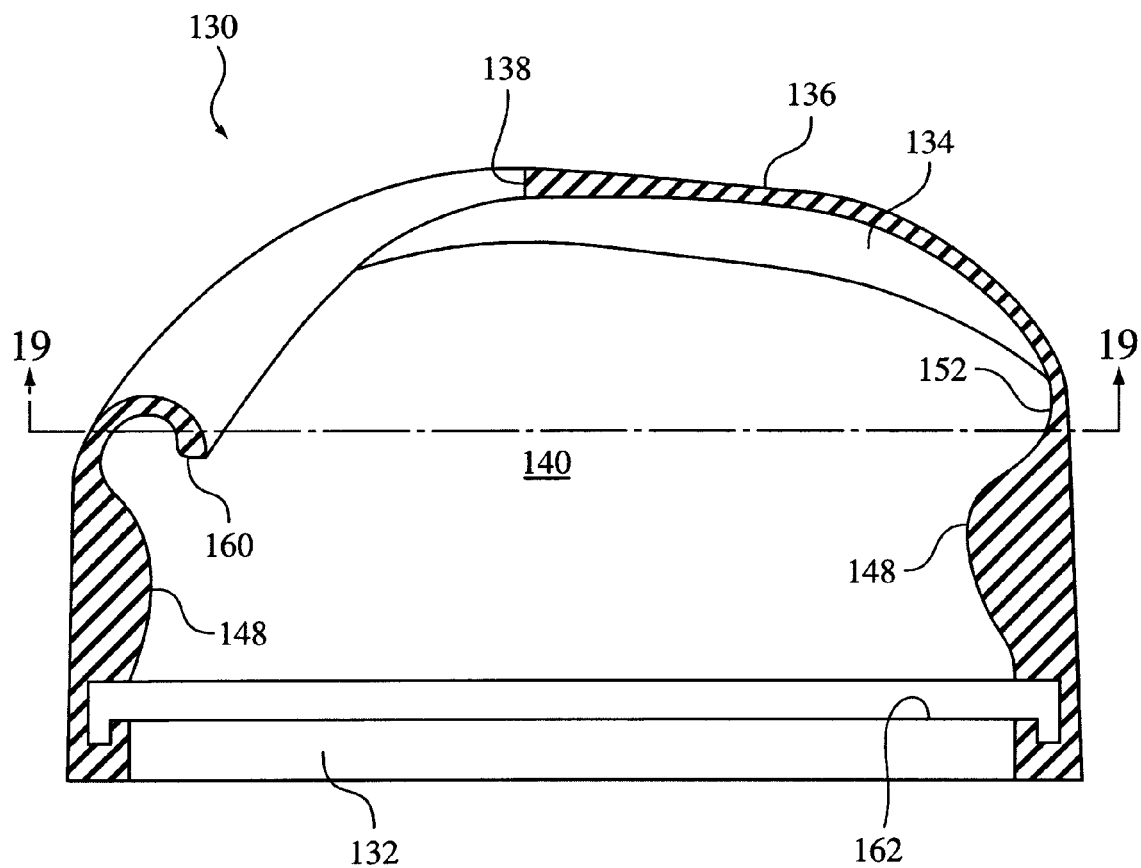
FIG. 17 is a cross-sectional view of the seal taken along line 17-17 of FIG. 15.
Figure 18:
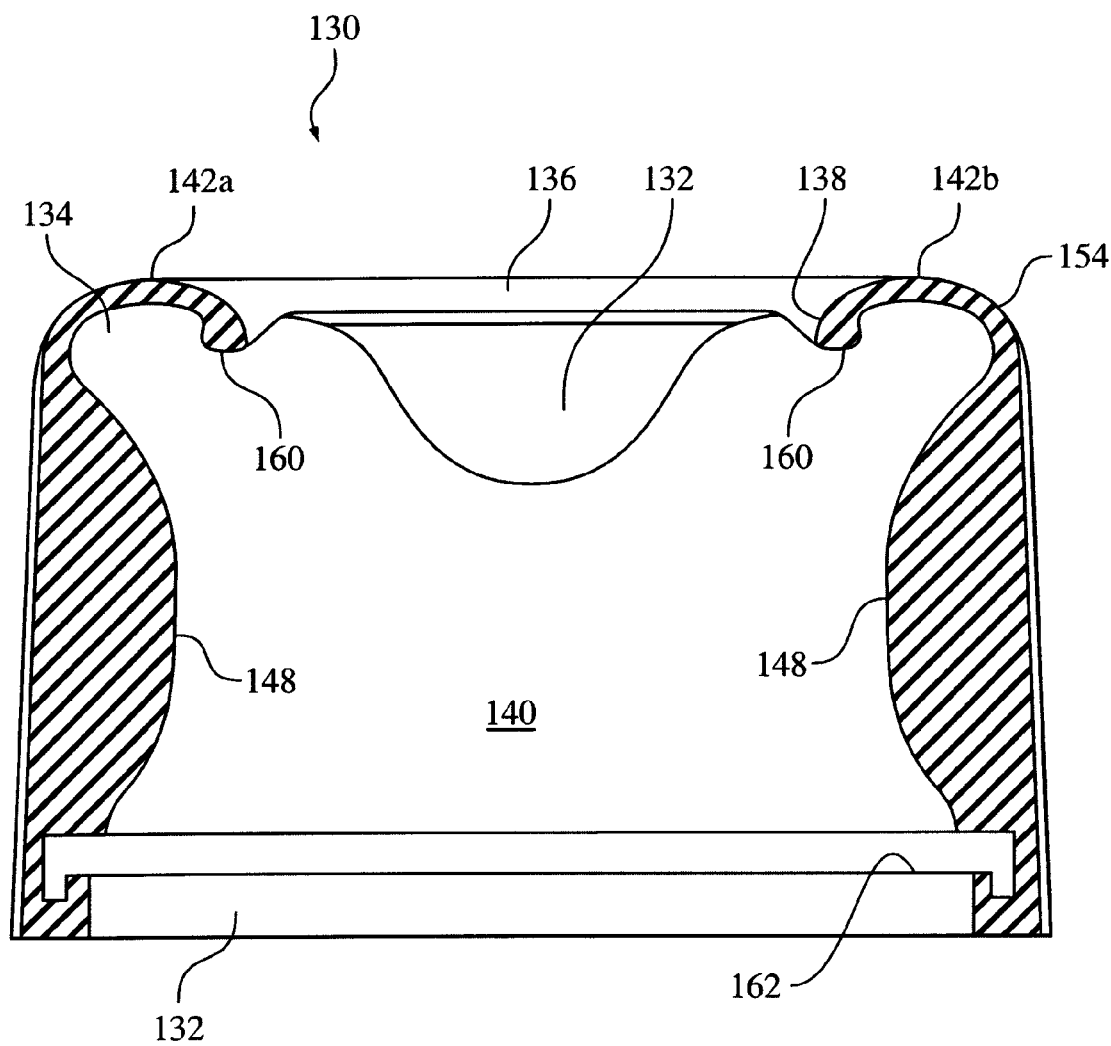
FIG. 18 is a cross-sectional view of the seal taken along line 18-18 of FIG. 16.
Figure 19:
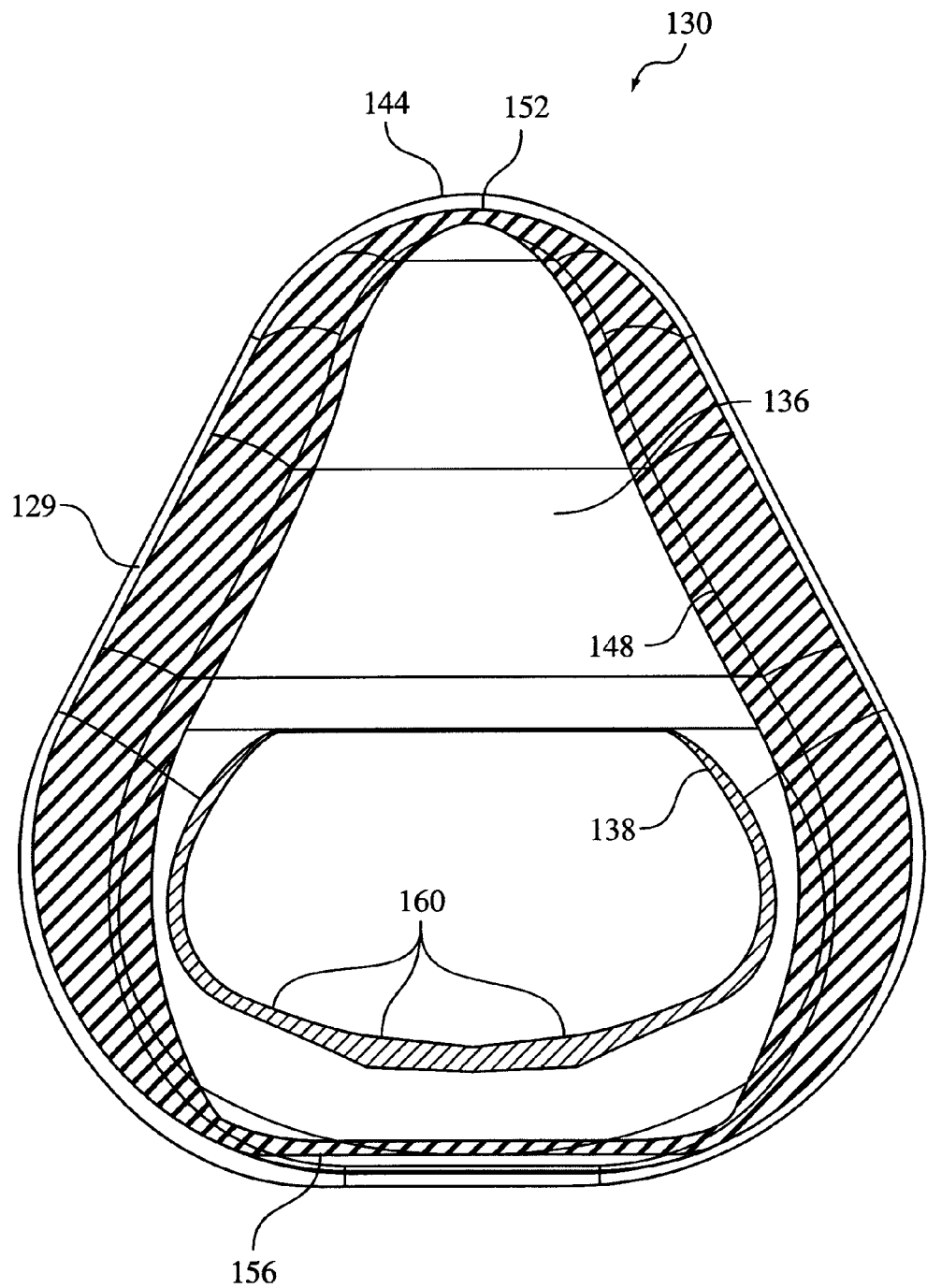
FIG. 19 is a cross-sectional view of the seal taken along line 19-19 of FIG. 17.
Figure 20:
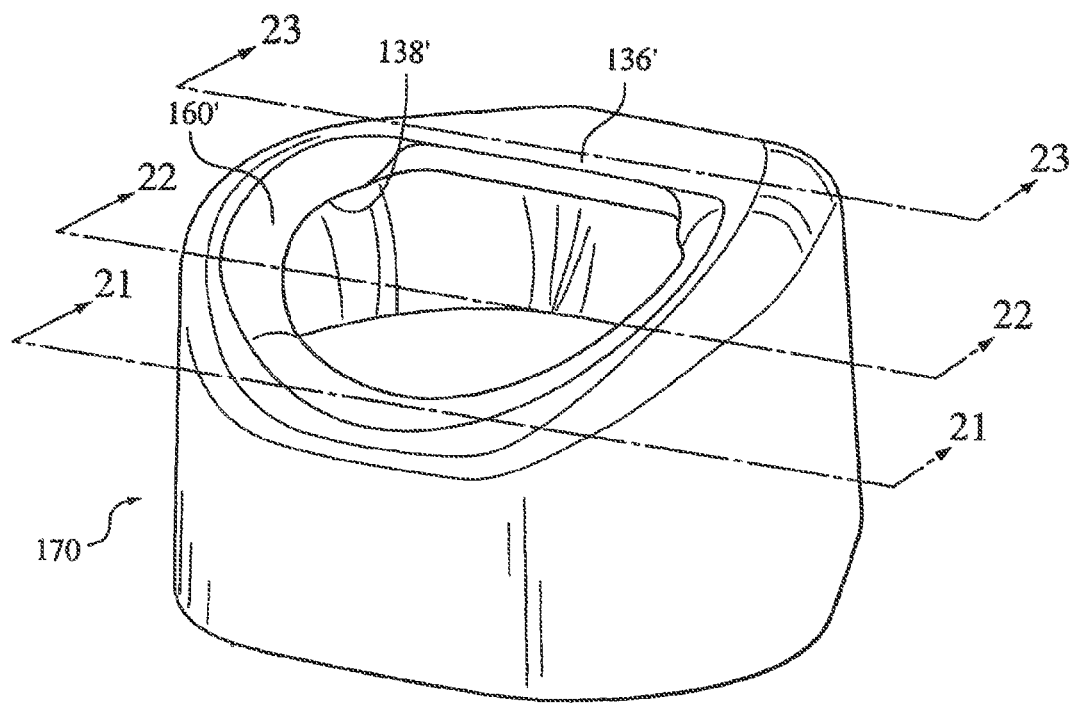
FIG. 20 is a front perspective view of a further embodiment for a seal according to the principles of the present invention.
Figure 21:
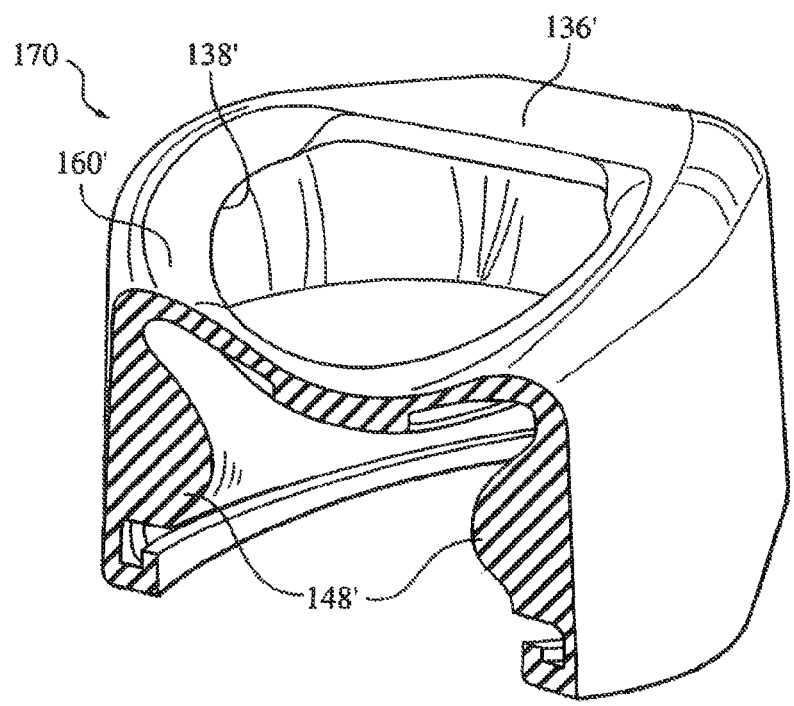
FIGS. 21, 22, and 23 are cross-sectional views of the seal of FIG. 20 taken along lines 21-21, 22-22, and 23-23 of FIG. 20, respectively.
Figure 22:
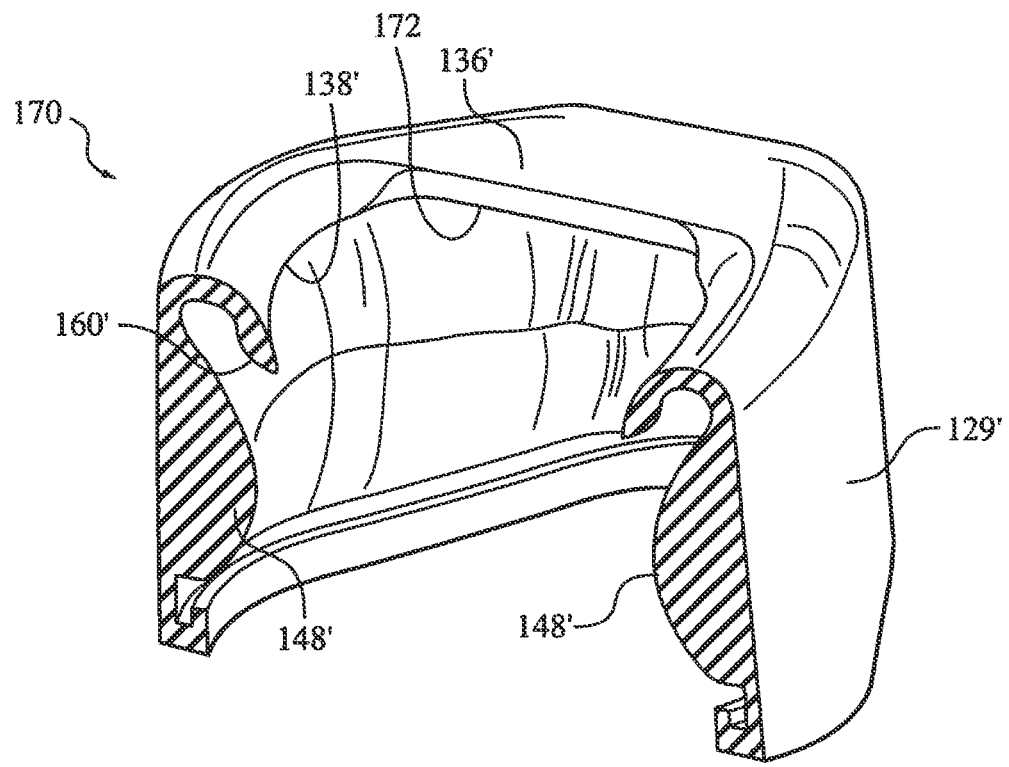
Figure 23:
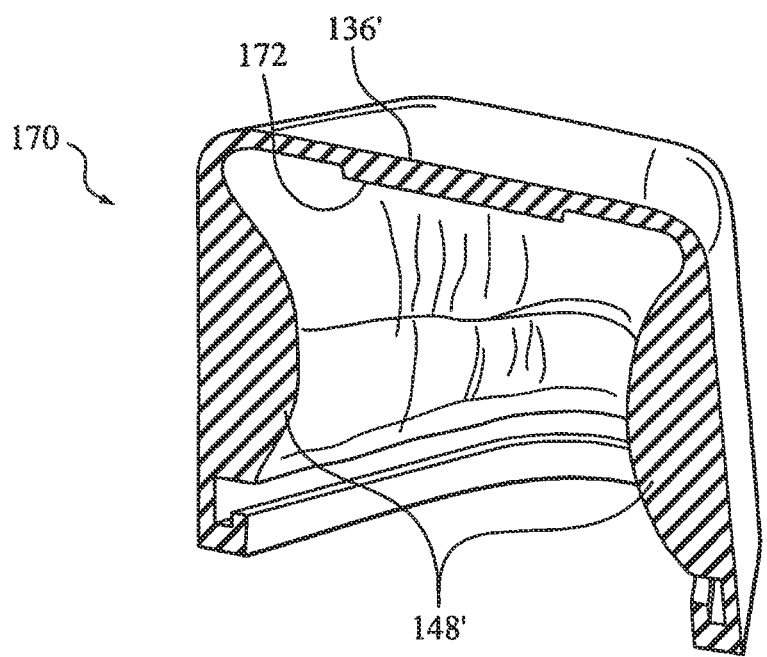

FIGS. 13 and 14 illustrate a seal 120 that is generally similar to seal 100 of FIGS. 10-12. A primary difference between seal 120 and seal 100 is the inclusion of two openings 122 in a flap 124 provided on a second end portion 126 of the seal. Each opening aligns with a nare of a user when the seal is donned by the patient. A small web of material 128 separates the opening 122.

FIGS. 15-19 illustrate a seal 130 according to a still further embodiment of the present invention. Like the seals discussed above, seal 130 includes a first end portion 132 that attaches to a mask body and a second end portion 134 that contacts a surface of a user. A flap 136 and an opening 138 are provided in the second end portion of the seal. Opening 138 communicates the user's airway with a cavity 140 defined by the seal.

In this embodiment, the second end portion of the seal, including flap 136, is generally planar. That is, second end portion 134 is not significantly contoured to match the human face or nose, as done in flap 112 in the previous embodiments. Flap 136 spans between sides 142a and 142b at the second end portion of the seal, terminates so as to define at least a portion of opening 138, and lies in a plane defined between these features and an apex 144 of the seal. The super-elastic nature of the flap allows it to stretch and conform to the user's face and nose with little resistance even without it being pre-shaped to correspond to the nose, as done in the seals of FIGS. 1-14. The result is a geometry free, highly forgiving seal that will fit a wide range of patients.

Sidewalls 129 of seal 130 are reinforced to ensure that the seal does not collapse when a compressive force is applied by the user on second end portion 134. In the illustrated exemplary embodiment, reinforcement of the sidewall is achieved by providing areas of increased thickness 148. It is to be understood that the present invention also contemplates providing other techniques for reinforcing the sidewalls, such as providing a stiffening member coupled to or disposed in the sidewall. The stiffening member can be attached using any conventional technique, such as by means of a mechanical attachment, an adhesive, or by molding the stiffening member to the sidewall, using, for example, a two-shot or over-molding process. The use of a separate stiffening member can be done alone or in combination with increasing the thickness of the seal. Seal support 16 from the previous embodiments is an example of one such stiffening member. The present invention also contemplates reinforcing the sidewall by providing the seal with different properties at the sidewall, such as making the sidewalls more rigid, for example, having an elongation property that is less than 1000%.

To allow for flexing of certain portions of the seal, the seal also includes areas of reduced thickness. For example, the present invention contemplates providing a thinned region 152 at apex 144 of the seal where it overlies the ridge of the nose. This area of the nose is especially sensitive to external pressure. Therefore, it is desirable to minimize the compressive force applied by the seal on this portion of the nose. This is accomplished by providing thinned region 152. Thinned regions 154 are also provided along the distal ends of sidewalls 129 to provide a flexible interface between the patient and the seal. In addition, a thinned region 156 is provided at a portion of the seal that overlies the area of the user between the upper lip and the bottom of the nose.

Seal 130 includes a rim 160 disposed around at least a portion of opening 138. Rim 160 flexes inward as a compressive force is applied on the distal, patient-contacting surface of second end portion 134. This allows for a comfortable fit of the seal against the user while also providing a good seal that minimizes gas leakage at the seal-patient interface.

In the illustrated embodiment, a channel 162 is provided at first end portion 132 of seal 130 to facilitate attachment of the seal to the mask body. It is to be understood that the present invention contemplates that channel 162 can have a variety of configurations, need not extend around the enter perimeter of the seal, can be provided on the external surface of the seal, and can be eliminated entirely if other techniques are used to mount the seal to the mask body.

FIGS. 20-23 illustrate a seal 180 according to a still further embodiment of the present invention. Seal 170 is similar in many respects to seal 130. One difference between these two seals resides in the configuration for rim 160' provided around opening 138'. Rim 160' is slightly longer than rim 160. Another difference resides in flap 136'. Flap 136' includes a slightly thickened portion 172 at a central portion of the flap and proximate to opening 138'. The thickened portion is provided to prevent the edge of the seal at the opening from vibrating as gas passes over the seal. These figures also serve to illustrate slightly different configurations for the sidewalls and help illustrate the features of the seal.

Figure 24:
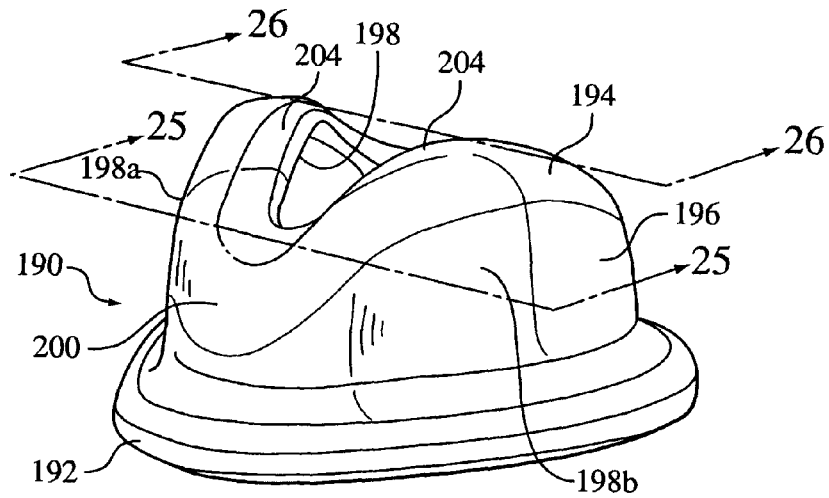
FIG. 24 is a front perspective view of another embodiment for a seal according to the principles of the present invention.
Figure 25:
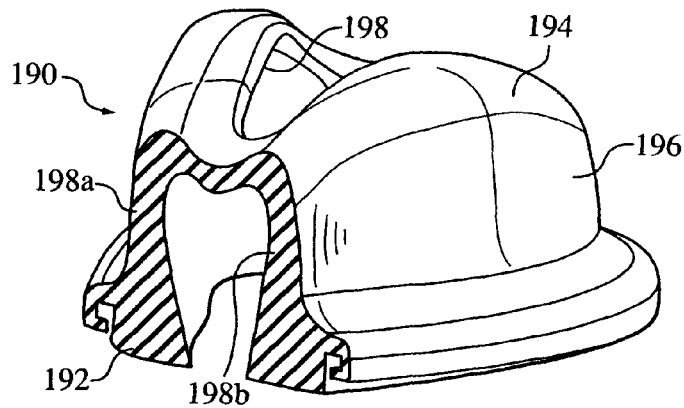
FIGS. 25 and 26 are cross-sectional views of the seal of FIG. 24 taken along lines 25-25 and 26-26 of FIG. 24, respectively.
Figure 26:
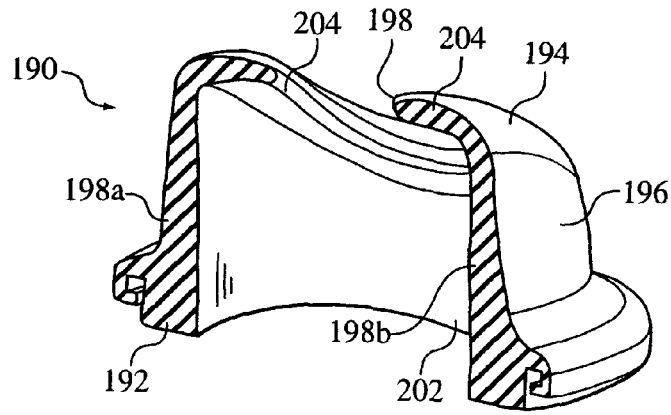

FIGS. 24-26 illustrate a seal 190 according to a still further embodiment of the present invention. Seal 190 includes a first end portion 192 that attaches to a mask body, a second end portion 194 that provides a patient contacting surface, and a sidewall 196 extending between the first and second end portions. An opening 198 is provided in the second end portion to communicate and airway of a patient with a chamber defined by the seal.

One significant difference between seal 190 and the other seals discussed herein is the configuration for the second end portion of the seal, i.e., the portion of the seal that contacts the patient. In this illustrated embodiment, second end portion 194 is contoured to generally match the facial features of a patient. For example, sides 198a and 198b have distal ends that are raised above an apex 200 and a lower portion 202 of the seal. In other words, sidewalls 196 are longer at sides 198a and 198b than at portions 200 and 202 so that the seal has a saddle-shape. It should also be noted that a thickness of the sidewalls and a rim 204 are more uniform than in the previous embodiment.

Figure 27:
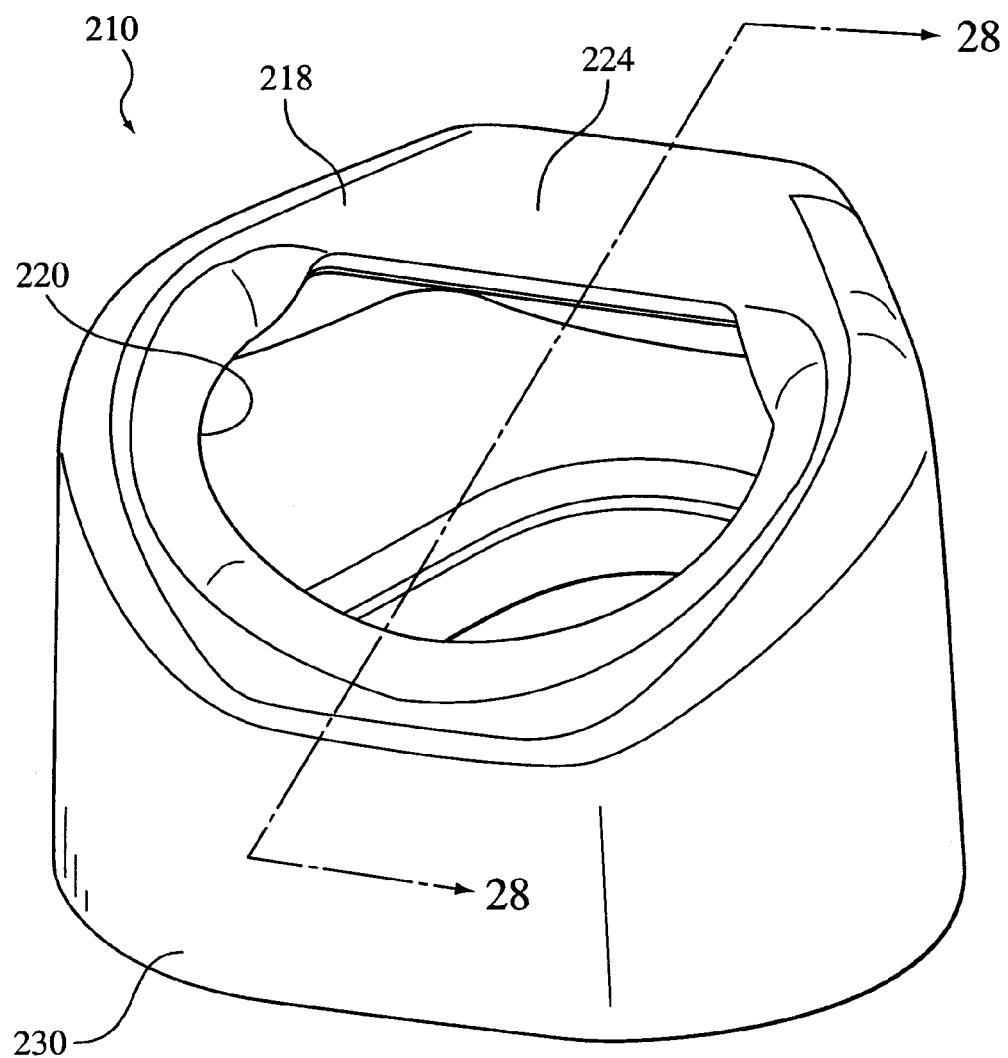
FIG. 27 is a front perspective view of yet another embodiment for a seal according to the principles of the present invention.
Figure 28:
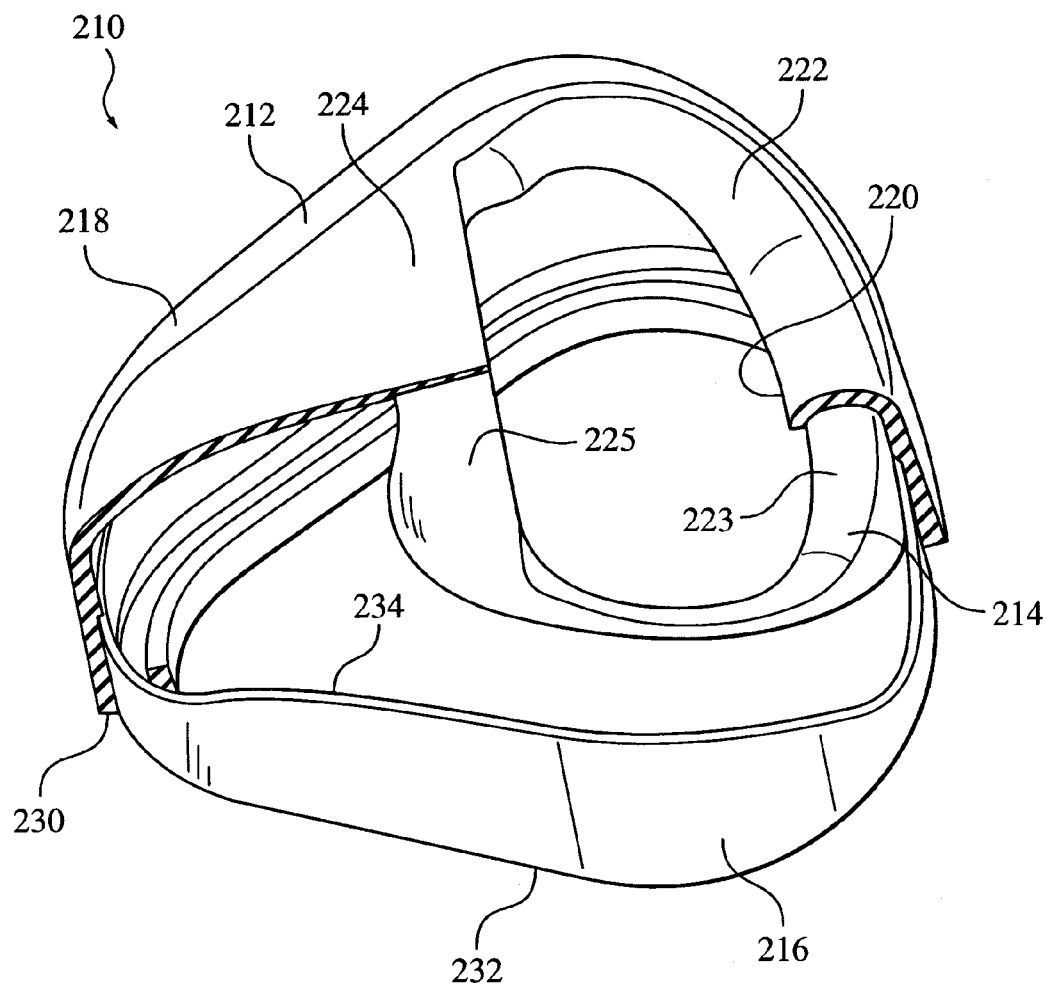
FIG. 28 is a side perspective view of the seal shown partially in section taken along line 28-28 of FIG. 27.
Figure 29:
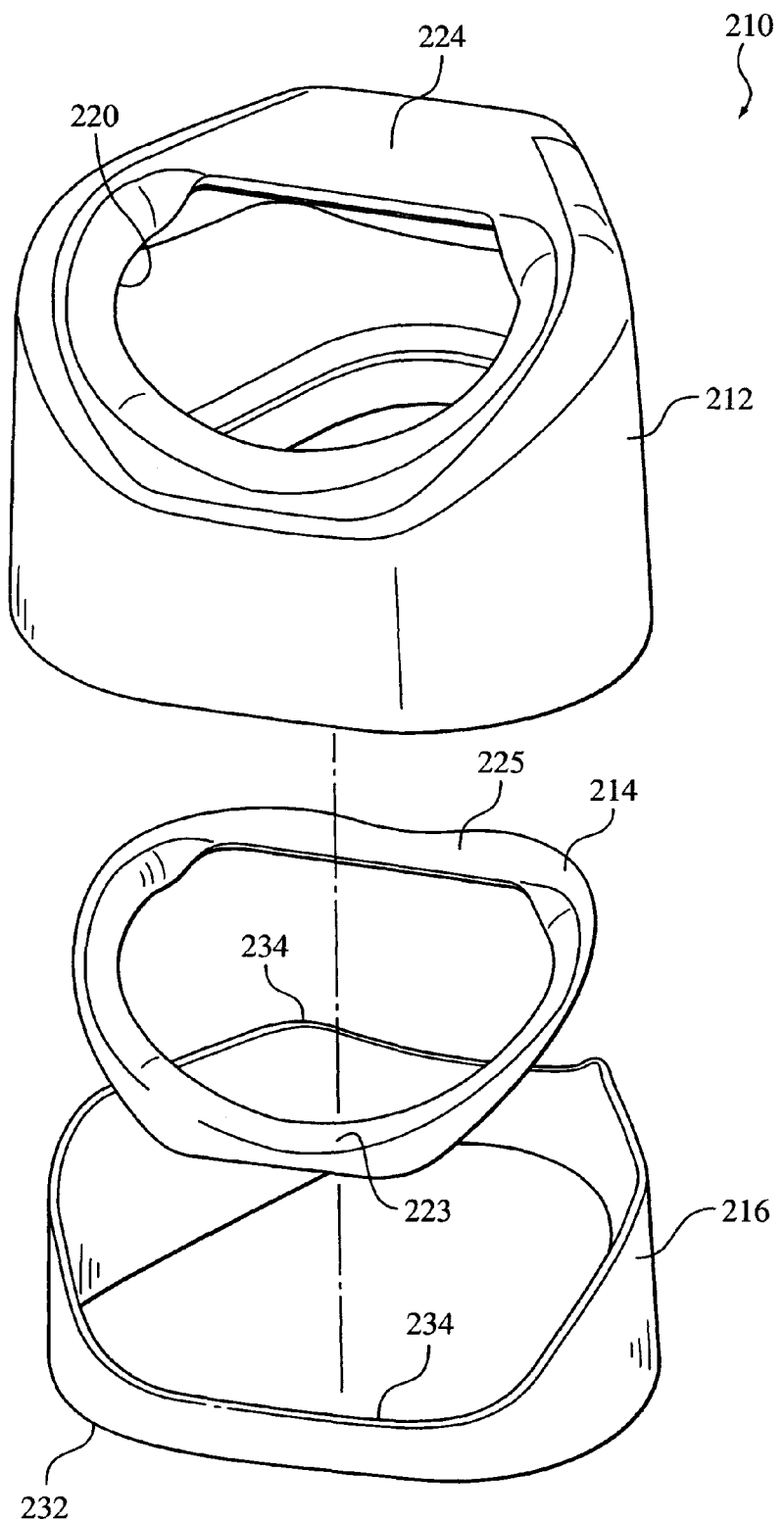
FIG. 29 is an exploded view of the seal of FIG. 27.

FIGS. 27-29 illustrate a seal 210 according to yet another embodiment of the present invention. In this embodiment, the seal is formed from more than one material, so that portions of the seal have supportive properties to maintain the structure of the seal while other portions of the seal provide the soft, comfortable feel that makes the seal particularly desirable to users. In this embodiment, seal 210 includes a seal portion 212, a first reinforcing portion 214, and a second reinforcing portion 216. The seal portion is preferably formed from a thermoplastic material having the characteristics discussed above. The first and second reinforcing portions are preferably formed from a reinforcing material that is less elastic than the thermoplastic material, i.e., having an elongation characteristic of less than 1000% and preferably in a range of 300-400%.

The present invention contemplates coupling first and second reinforcing portions 214 and 216 to seal portion 212 in any suitable manner to form an integrated homogeneous seal. However, in a presently preferred exemplary embodiment, the first and second reinforcing portions are joined with the seal portion using a two-shot molding process. Of course, other techniques for attaching the seal portion to the first and second reinforcing portions are possible, such as heat sealing the members together, attaching these components using an adhesive, or using any combination of these bonding techniques.

It should be noted that the two-shot molding process does more than just provide sidewall reinforcement. It allows the binding of two similar materials, such as two materials that are elastomer in nature, in one wall section to locally alter the properties of the mask in that particular section. It is different from other conventional sidewall reinforcement techniques, such as using a rigid support either internal or external to the seal and/or providing thickened wall sections. Two-shot molding provides continuity in the form of the seal and it does not add weight. Two-shot molding and over-molding are common in thermoplastic forming, but they are often made possible with rigid substrates or one elastic material on a rigid substrate.

As best shown in FIG. 28, first reinforcing portion 214 attaches to the seal generally at a second end portion 218 of the seal. More specifically, first reinforcing portion 214 is a generally annular piece of material that is disposed around a perimeter of an opening 220 in second end portion 218. As with the previous embodiments, opening 200 communicates an airway of the user with the interior of the seal. Providing first reinforcing portion 214 around opening 220 enhances the structural integrity of the seal around the opening and helps prevent vibration of the edge of the seal at the opening as gas passes over the seal. In the illustrated embodiment, first reinforcing portion 214 is contoured to correspond to the contour of the seal around the opening, including providing a rolling shape that generally matches an arcuate or semi-circular shape of a rim 222 at a first portion 223 and a flat shape that matches a planar shape of a flap 224 at a second portion 225.

Second reinforcing portion 216 is provided generally at first end portion 230 of seal 210. In the illustrated embodiment, second reinforcing portion 216 is an annular ring-shape member having a relatively thin wall structure. It includes a first edge 232 that matches a corresponding edge of first end portion 230 and a second edge 234. Second edge is preferably contoured to provide increased support at selected locations along the perimeter of the seal. That is, the height of second reinforcing portion 216 is selected to be larger where more support is desired, such as at the side of the seal, and less where less support is need, such as at the area of the seal that sits above the user's upper lip.

It is to be understood that first and second reinforcing portions 214 and 216 can have a variety of other sizes and configurations. The present invention also contemplates providing other reinforcing portions for the seal or eliminating either the first or the second reinforcing portion depending on what structural support is desired for the seal. In addition, the reinforcing portions need not be defined by any member, but can be any shape that provides the desired support function for the seal.

Figure 30:
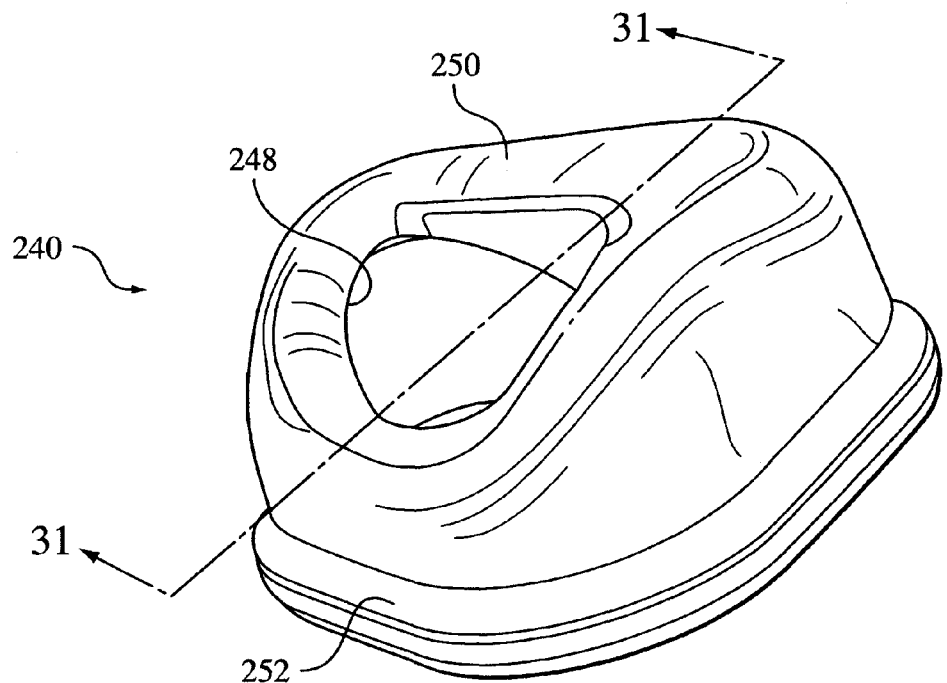
FIG. 30 is a front perspective view of yet another embodiment for a seal according to the principles of the present invention.
Figure 31:
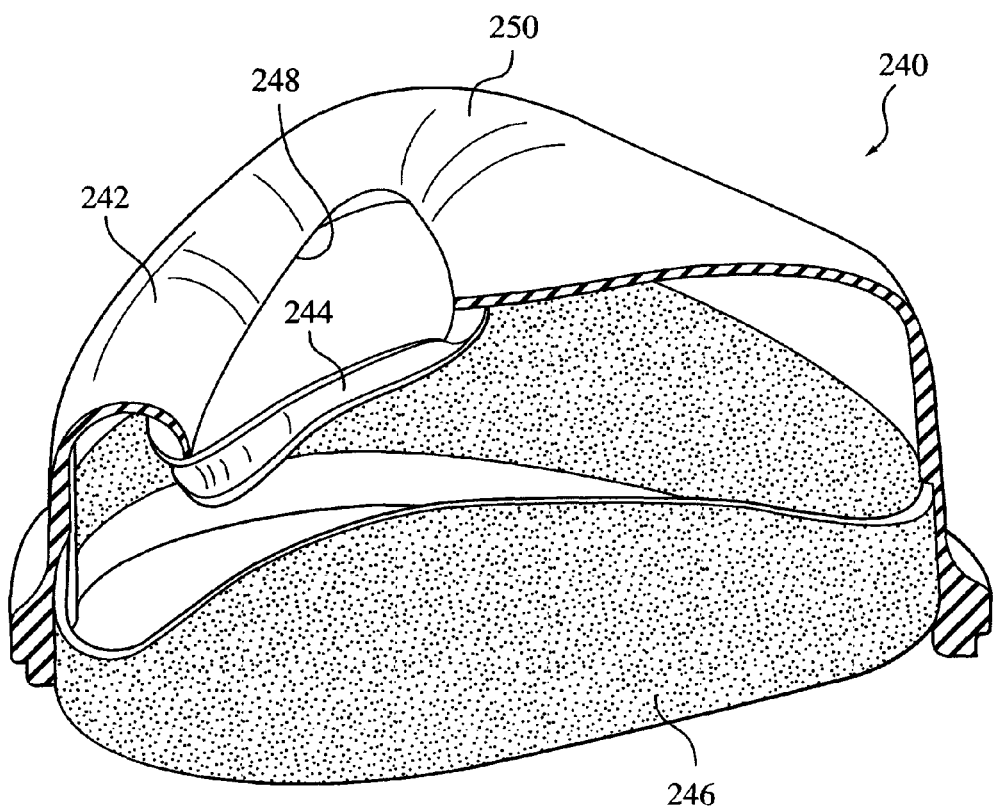
FIG. 31 is a side perspective view of the seal shown partially in section taken along line 31-31 of FIG. 30.
Figure 32:
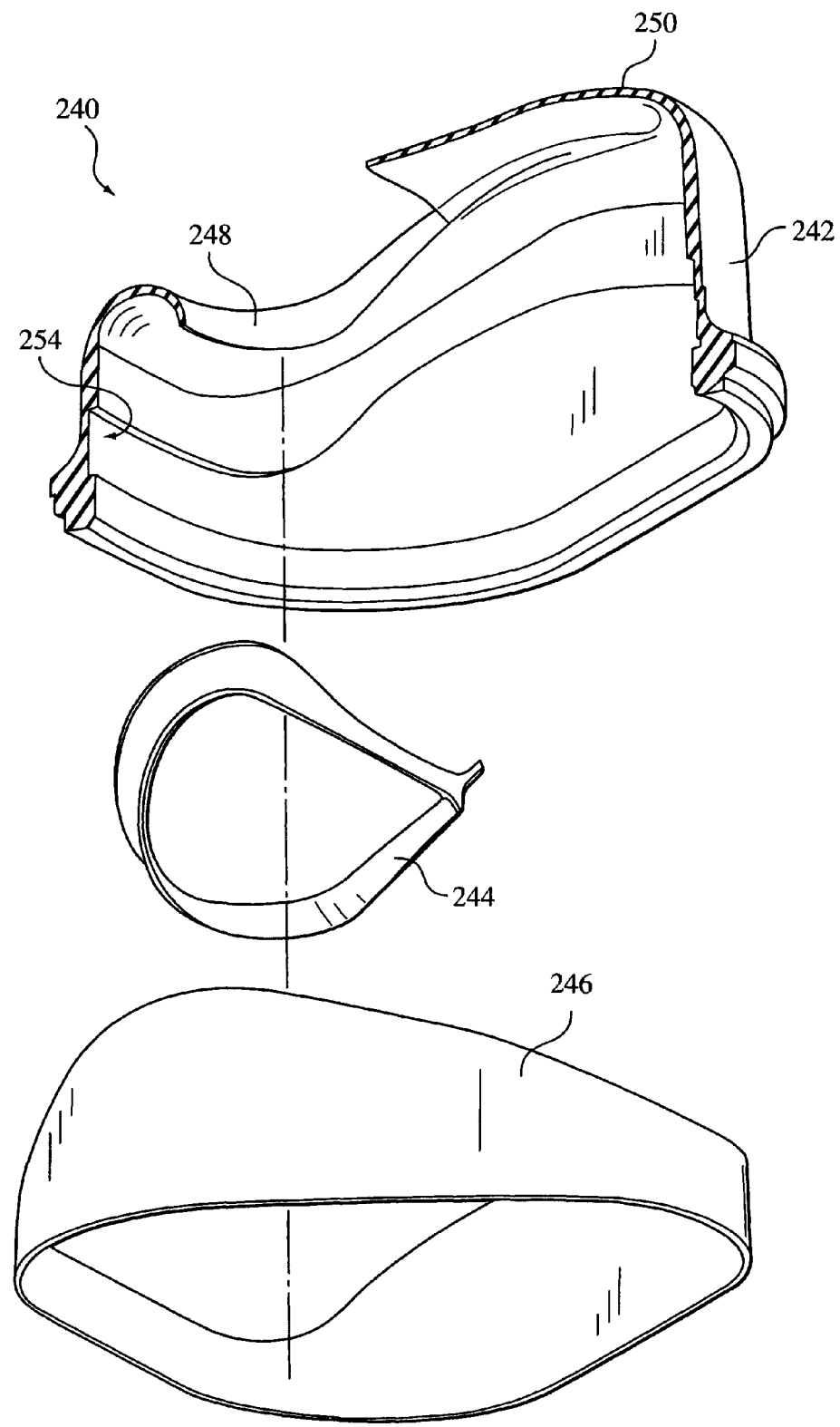
FIG. 32 is an exploded view of the seal of FIG. 30.

FIGS. 30-32 illustrate yet another embodiment for a seal 240 according to the principles of the present invention. Seal 240 is generally similar to seal 210 in that it is formed from multiple components coupled together. More specifically, seal 240 is comprised of a seal portion 242, a first reinforcing portion 244, and a second reinforcing portion 246. As with the previous embodiment, first reinforcing portion 244 is coupled to seal portion 242 in an area surrounding an opening 248 provided in second end portion 250 of the seal to provide structural support around the opening. Second reinforcing portion 246 is provided at another end of the seal generally at a first end portion 252 where the seal couples to a mask body. FIGS. 30-32 serve to illustrate that the present invention contemplates that the components of the seal can take on a myriad of shapes, sizes, and configurations, while still falling within the principles of the present invention.

As perhaps best shown in FIG. 32, the present invention also contemplates providing a channel 254 defined in an interior surface of seal portion 242 to receive, at least partially, second reinforcing portion 246. It should be noted that a similar channel can be provided in the seal for the first reinforcing portion.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A respiratory mask comprising:
   (a) a mask body;
   (b) a cushion operatively coupled to the mask body such that a cavity is defined in the cushion, wherein the cavity is adapted to receive a portion of a user, responsive to the respiratory mask being disposed on such a user, the cushion comprising:
      (1) a first end portion adapted to be coupled to the mask body,
      (2) a second end portion adapted for sealing engagement with a face of a user, wherein the second end portion of the cushion is configured to contact a surface of such a user when the respiratory mask is donned by such a user, and
      (3) a sidewall extending between the first end portion and the second end portion, wherein at least one of the first end portion, the second end portion, and the sidewall is formed from an elastomeric material having an elongation of at least 1000%, and wherein the sidewall of the cushion extends from the mask body along a first plane; and (c) a first support member formed from a rigid or semi-rigid material and operatively coupled to the mask body, the first support member comprising:
   (1) a first end portion adapted to be coupled to the mask body,
   (2) a second end portion distal from the first end portion, and
   (3) a support sidewall extending between the first end portion and the second end portion, and wherein the support sidewall of the first support member extends from the mask body along a second plane that is general parallel to the first plane.

2. The mask of claim 1, wherein the first support member formed at least in part from a plastic, ABS, EVA copolymer, polypropylene, HDPE, PE, PVC, or polyurethane.

3. The mask of claim 1, wherein the first end portion of the first support member is generally annular and is configured to have a shape that is substantially similar to an edge portion of the mask body to which the first end portion of the first support member is attached.

4. The mask of claim 1, wherein the second end portion of the first support member is defines a generally annular contoured surface that approximates surface contours of a user's facial structure.

5. The mask of claim 1, wherein at least a portion of the support sidewall and the second end portion of the first support member are disposed within the cushion.

6. The mask of claim 1, wherein the first support member is disposed proximate to the cushion on a first side of the cushion proximate to the cavity such that the first support member prevents at least a portion of the cushion from moving toward the cavity.

7. The mask of claim 6, further comprising a second support member disposed proximate to the cushion on a second side of the cushion opposite the first side.

8. The mask of claim 1, wherein the first support member is disposed proximate to the cushion on a second side of the cushion opposite to the cavity such that the first support member prevents at least a portion of the cushion from moving away from the cavity.

9. The mask of claim 8, further comprising a second support member disposed proximate to the cushion on a first side of the cushion opposite the second side.

10. The mask of claim 1, wherein the elastomeric material of the cushion includes at least one of the following properties:
   a durometer in a range of 10-50 on a shore 00 scale,
   a 300% Modulus in a range of 10-15 PSI, or
   a tear strength in a range of 40-50 PLI.

11. The mask of claim 1, wherein the sidewall of the cushion includes an area of increased thickness with respect to a remainder of the sidewall of the cushion.

12. The mask of claim 1, further comprising a retaining portion that secures the cushion to the mask body.

13. The mask of claim 1, wherein at least one of the first end portion of the first support member, the second end portion of the first support member, and the support sidewall is formed from an elastomeric material having an elongation of less than 1000%.

14. The mask of claim 1, wherein the support sidewall of the first support member includes an elastomeric material having an elongation of less than 1000%.

* * * * *